(12) United States Patent
Lipkowska et al.

(10) Patent No.: US 8,541,365 B2
(45) Date of Patent: Sep. 24, 2013

(54) DENDRIMERIC COMPOUNDS COMPRISING AMINO ACIDS, HYPERBRANCHED CORE COMPOUND, PROCESS FOR PREPARATION OF DENDRIMERIC COMPOUNDS COMPRISING AMINO ACIDS AND HYPERBRANCHED CORE COMPOUND, AND USE THEREOF

(75) Inventors: Zofia Lipkowska, Warszawa (PL); Piotr Polcyn, Warzawa (PL); Andrzej Wojciech Lipkowski, Warszawa (PL)

(73) Assignee: Instytut Chemii Organicznej, Polska Akademia Nauk, Warszawa (PL)

( * ) Notice: Subject to any disclaimer, the term of this patent is extended or adjusted under 35 U.S.C. 154(b) by 194 days.

(21) Appl. No.: 13/062,186

(22) PCT Filed: Sep. 18, 2009

(86) PCT No.: PCT/PL2009/000090
§ 371 (c)(1),
(2), (4) Date: Mar. 3, 2011

(87) PCT Pub. No.: WO2010/033043
PCT Pub. Date: Mar. 25, 2010

(65) Prior Publication Data
US 2011/0152175 A1 Jun. 23, 2011

(30) Foreign Application Priority Data

Sep. 22, 2008 (PL) .......................... 386123

(51) Int. Cl.
A61K 38/00 (2006.01)
C07K 7/06 (2006.01)
(52) U.S. Cl.
USPC .......................................... 514/2.4
(58) Field of Classification Search
None
See application file for complete search history.

(56) References Cited

FOREIGN PATENT DOCUMENTS
PL 197752 B1 3/2005

OTHER PUBLICATIONS

International Journal of Pharmaceutics, 2006, 309, 208-217.*
Janiszewska et al. Low Molecular Mass Peptide Dendrimers that Express Antimicrobial Properties. Bioorganic & Medicinal Chemistry Letters. 2003. vol. 13. pp. 3711-3713.

Janiszewska et al. Amphiphilic Dendrimeric Peptides as Model Non-Sequential Pharmacophores with Antimicrobial Properties. Journal of Molecular Microbiology and Biotechnology. 2007. vol. 13. pp. 220-225.
Klajnert et al. Biological properties of low molecular mass peptide dendrimers. International Journal of Pharmaceutics. 2006. vol. 309. pp. 208-217.

* cited by examiner

*Primary Examiner* — Marcela M Cordero Garcia
*Assistant Examiner* — Kaipeen Yang
(74) *Attorney, Agent, or Firm* — Marsh Fischmann & Breyfogle LLP

(57) ABSTRACT

The invention provides dendrimeric compounds of the formula 1 comprising amino acids, wherein n is an integer of 1-4, T is an alkylidene —(CH2)2CONH(CH2)2- group, R2 is an —NH2 group or a moiety of a primary organic amine, and P is an amino acid and/or peptide moiety, wherein at least one hydrogen atom of at least one amino group is optionally replaced by a protective group, and a hyperbranched core compound of the formula 3, wherein T and R2 are as defined above. The invention provides also a process for the preparation of a dendrimeric compound and a hyperbranched core, wherein the process employs addition reactions of alkyl acrylate and a basic amino acid, and use of a hyperbranched core for the preparation of a dendrimeric compound comprising amino acids. The invention provides also use of dendrimeric compounds for the preparation of the medicament for inhibiting growth of bacterial cells, fungi and tumor cells.

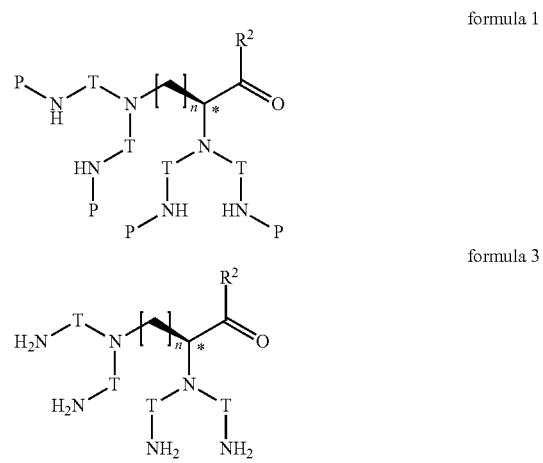

28 Claims, No Drawings

DENDRIMERIC COMPOUNDS COMPRISING AMINO ACIDS, HYPERBRANCHED CORE COMPOUND, PROCESS FOR PREPARATION OF DENDRIMERIC COMPOUNDS COMPRISING AMINO ACIDS AND HYPERBRANCHED CORE COMPOUND, AND USE THEREOF

The invention provides dendrimeric compounds comprising amino acids, a hyperbranched core compound, a process for the preparation of the dendrimeric compounds comprising amino acids and a process for the preparation of the hyperbranched core compound, and use of the dendrimeric compounds comprising amino acids and the hyperbranched core compound.

Dendrimers and synthesis methods for dendrimers are known, wherein the dendrimeric structure is based on use of small achiral molecules, such as ammonia, ethylenediamine, propylenediamine or benzene derivatives. L. J. Twyman et al., in *J. Chem. Res. Miniprint;* 12, 1998, 3408 disclose a process for designing novel central molecules for dendrimer synthesis.

The Polish patent PL 197752 discloses novel compounds with dendrimeric structure, including peptide fragments in the branches, that exhibit bacteriostatic and antifungal properties. A core of the molecule is prepared on the basis of aliphatic amino acids with two amino groups, i.e. basic amino acids, such as lysine (Lys) or ornithine (Orn). Amino groups comprise attachment points for consecutive amino acid and/or peptide moieties which generate branches of the dendrimer structure. The compounds and biological activities thereof were also presented in *J. Mol. Microbiol. Biotechn.* (13, 2007, 220-225).

Coupling reactions with successive amino acids/peptides allow for double branching only in each reaction cycle. (See Klajnert B., J. Janiszewska, Urbanczyk-Lipkowska Z, Bryszewska M., Shcharbin D., Labieniec M.: "Biological properties of low molecular mass peptide dendrimers", *Intern. J Pharmaceutics* 309 (2006)208-217].

The invention provides dendrimeric compounds comprising amino acids, a hyperbranched core compound, a process for the preparation of the dendrimeric compounds comprising amino acids, and a process for the preparation of the hyperbranched core compound, and use of the dendrimeric compounds comprising amino acids and the hyperbranched core compound.

Dendrimeric compounds comprising amino acids according to the invention are represented by the formula 1

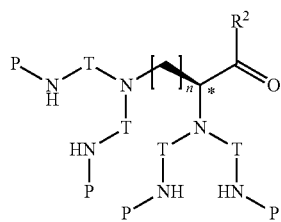

formula 1 and include a branched core with four -T-NH— branches, wherein T is an alkylidene group —$(CH_2)_2CONH(CH_2)_2$—, and one $R^2$ branch, wherein $R^2$ is an —$NH_2$ group, or a moiety derived from a primary organic amine molecule by removing a hydrogen atom from an amino group, and have at least four terminal fragments P, wherein P is an amino acid and/or peptide moiety derived from an amino acid/peptide molecule by removing a hydroxy group from a carboxy group, at least one hydrogen atom of at least one amino group in the amino acid/peptide moiety being optionally replaced by a protective group.

Preferably, the compounds are represented by the formula 2

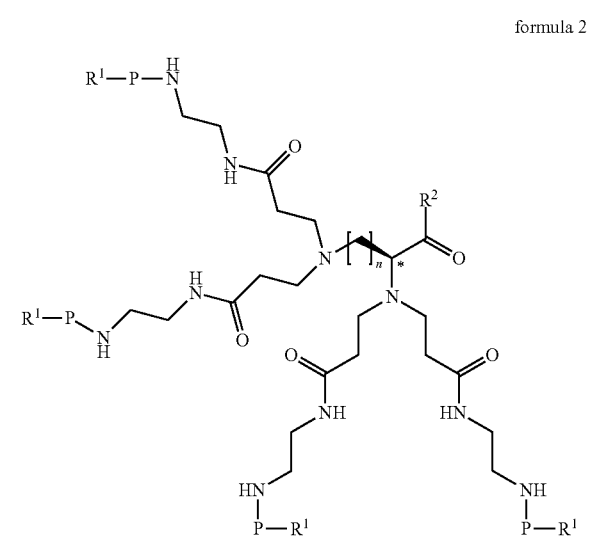

formula 2 wherein n is an integer of from 1 to 4 inclusive

P is a moiety derived from an amino acid molecule with two amino groups, by removing a hydroxy group from a carboxy group, at least one hydrogen atom of at least one amino group being optionally replaced by an $R^1$ substituent selected from the group comprising: fatty alkylcarbonyl, fatty alkenylcarbonyl, alkoxycarbonyl, arylalkoxycarbonyl optionally substituted on the aryl by halo, arylsulfonyl substituted on the aryl by alkylamino group; a moiety derived from an amino acid molecule with two amino groups, by removing a hydroxy group from a carboxy group, at least one hydrogen atom of at least one amino group being optionally replaced by a substituent selected from the group comprising fatty alkylcarbonyl, fatty alkenylcarbonyl, alkoxycarbonyl, arylalkoxycarbonyl optionally substituted on the aryl by halo, arylsulfonyl substituted on the aryl by alkylamino group; or a moiety derived from a lysine, ornithine, 2,4-diaminobutyric acid or 2,3-diaminopropionic acid amino acid molecule, by removing a hydroxy group from a carboxy group;

$R^2$ is a substituent independently selected from the group comprising an amino substituent, a substituent derived from an amide or $C_{1-6}$ alkyl ester of a natural amino acid by removing a hydrogen atom from an amino group, a substituent derived from $C_{1-6}$ alkyl ester of a linear or branched chain non-natural $C_{3-6}$ aliphatic amino acid by removing a hydrogen atom from an amino group, as well as a substituent derived by removing a hydrogen atom from an amino group of a tryptamine, benzylamine optionally substituted by alkyl, phenylamine optionally substituted by nitro, aminopyridine, histamine, $C_5$-$C_{22}$ aliphatic amine, aminocoumarin, or cholesterylamine molecule.

In particular, the compounds are in the form of a cationic salt with a pharmaceutically acceptable anion. The compounds are particularly in the form of hydrochloride salts.

Preferably, the compounds are represented by the formula 2, wherein:

n is an integer of from 1 to 4 inclusive,

P is a moiety derived from an amino acid molecule, in a D or L form, by removing a hydroxy group from a carboxy group of lysine, ornithine, arginine, 1,4-diaminobutyric acid (DAB), or 1,3-diaminopropionic acid (DAP), at least one hydrogen atom of at least one amino group being optionally replaced by an $R^1$ substituent, $R^1$ is a substituent independently selected from the group comprising a hydrogen atom (H), benzyloxycarbonyl (Z), 2-chlorobenzyloxycarbonyl (2-Cl—Z), 2-bromo-benzyloxycarbonyl (2-Br—Z), 2-iodobenzyloxycarbonyl (2-I—Z), t-butyloxycarbonyl (Boc), fatty alkylcarbonyl, fatty alkenylcarbonyl, dansyl (DNS), naphthylsulfonyl, 9-fluorenyl-methoxycarbonyl (Fmoc), and moieties derived by removing a hydroxy group from a carboxy group of the following molecules: Lysine (Lys), D-Lysine (D-Lys), Z-Lys, Z-D-Lys, Lys-(ε-Z), D-Lys-(ε-Z), (2-Cl—Z)-Lys, (2-Cl—Z)-D-Lys, Lys-(ε-2-Cl—Z), D-Lys-(ε-2-Cl—Z), DNS-(Lys), Lys-(ε-DNS), or Z-Arg, Z-D-Arg, (2-Cl—Z)-Arg, (2-Cl—Z)-D-Arg, Lys-(Z)Lys[Lys-(Z)], D-Lys-(Z)Lys[D-Lys-(Z)], Lys-(Z)Orn[Lys-(Z)], D-Lys-(Z)Orn[D-Lys-(Z)], Z-Lys-Lys-[Z-Lys], Z-Lys-D-Lys-[Z-Lys], Z-D-Lys-Lys-[Z-D-Lys], Z-D-Lys-D-Lys-[Z-D-Lys], derivatives with analogous sequences, wherein the starting lysine moiety is replaced by an ornithine moiety (Orn), derivatives with analogous sequences, wherein the starting lysine moiety is replaced by a 2,4-diaminobutyric acid (DAB) moiety, derivatives with analogous sequences, wherein the starting lysine moiety is replaced by a 2,3-diaminopropionic acid (DAP) moiety, Z-Arg-Lys[Z-Arg], Z-D-Arg-Lys[Z-D-Arg], Z-Arg-Orn [Z-Arg], Z-D-Arg-Orn[Z-D-Arg], Z-Arg-D-Lys-[Z-Arg], Z-D-Arg-D-Lys[Z-D-Arg], Z-Arg-D-Orn-[Z-Arg], Z-D-Arg-D-Orn[Z-D-Arg], (2-Cl—Z)-Arg-Lys[(2-Cl—Z)-Arg], (2-Cl—Z)-D-Arg-Lys[(2-Cl—Z)-D-Arg], (2-Cl—Z)-Arg-Orn[(2-Cl—Z)-Arg], (2-Cl—Z)-D-Arg-Orn[(2-Cl—Z)-D-Arg], (2-Cl—Z)-Arg-D-Lys-[(2-Cl—Z)-Arg], (2-Cl—Z)-D-Arg-D-Lys[(2-Cl—Z)-D-Arg], (2-Cl—Z)-Arg-D-Orn-[(2-Cl—Z)-Arg], (2Cl—Z)-D-Arg-D-Orn[(2-Cl—Z)-D-Arg], $R^2$ is a substituent independently selected from the group comprising an amino substituent, a substituent derived from an amide or $C_{1-6}$alkyl ester of Phe, D-Phe, Tyr, D-Tyr, Ala, D-Ala, Gly, Ile, D-Ile, L and D-Trp by removing a hydrogen atom from an amino group, a substituent derived from $C_{1-6}$alkyl ester of a linear $C_{3-6}$aliphatic amino acid by removing a hydrogen atom from an amino group, as well as a substituent derived by removing a hydrogen atom from an amino group of a tryptamine, methylbenzylamine, benzylamine, nitrophenylamine, phenylamine, aminopyridine, histamine, $C_5$-$C_{22}$aliphatic amine, 7-aminocoumarin, cholesterylamine, or glucosamine molecule.

In particular, the compounds of the formula 2 are the following:

the compound of the formula 2, wherein n is 4, P—$R^1$ is $N^\alpha$-2-chlorobenzyloxy-carbonyl-L-Arg and $R^2$ is a 3-aminopyridine moiety $C_5H_4N$—NH—, with the L-configuration on the chiral carbon atom linked to the —C(O)$R^2$ group, the compound of the formula 2, wherein n is 3, P—$R^1$ is $N^\epsilon$-2-chlorobenzyloxy-carbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 3, P—$R^1$ is $N^\alpha$-2-chlorobenzyloxy-carbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 2, P—$R^1$ is $N^\alpha$-2-chlorobenzyloxy-carbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 2, P—$R^1$ is $N^\epsilon$-2-chlorobenzyloxycarbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 3, P—$R^1$ is $N^\epsilon$-2-chlorobenzyloxy-carbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 1, P—$R^1$ is $N^\alpha$-2-chlorobenzyloxycarbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 4, P—$R^1$ is $N^\alpha$-2-chlorobenzyloxy-carbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 4, P—$R^1$ is $N^\alpha$-benzyloxycarbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 4, P—$R^1$ is $N^\epsilon$-benzyloxycarbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 4, P—$R^1$ is $N^\alpha$-2-bromobenzyloxy-carbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 4, P—$R^1$ is $N^\alpha$-benzyloxycarbonyl-L-DAP and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 4, P—$R^1$ is $N^\alpha$-2-chlorobenzyloxy-carbonyl-L-Orn and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 3, P—$R^1$ is $N^\alpha$-2-chlorobenzyloxy-carbonyl-L-Lys and $R^2$ is a histamine moiety $C_3H_3N_2$—$CH_2$—$CH_2$—NH—, with the L-configuration on the chiral carbon atom linked to the —C(O)$R^2$ group, in a hydrochloride salt form, the compound of the formula 2, wherein n is 3, P—$R^1$ is $N^\epsilon$-2-chlorobenzyloxy-carbonyl-L-Lys and $R^2$ is a histamine moiety $C_3H_3N_2$—$CH_2$—$CH_2$—NH—, with the L-configuration on the chiral carbon atom linked to the —C(O)$R^2$ group, in a hydrochloride salt form, the compound of the formula 2, wherein n is 3, P—$R^1$ is $N^\alpha$-2-chlorobenzyloxy-carbonyl-L-Lys and $R^2$ is a dodecylamine moiety $C_{12}H_{25}NH—$, with the L-configuration on the chiral carbon atom linked to the —$C(O)R^2$ group, in a hydrochloride salt form.

The hyperbranched core compound according to the invention is represented by the formula 3

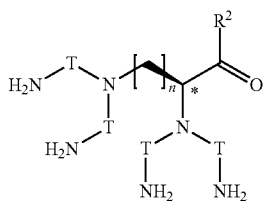

formula 3 and it has four -T-$NH_2$ branches, wherein T is an alkylidene group —$(CH_2)_2CONH(CH_2)_2$—, and one $R^2$ branch, wherein $R^2$ is an —$NH_2$ group or a moiety derived from a primary organic amine molecule, by removing a hydrogen atom from an amino group.

Preferably, the compound is represented by the formula 4

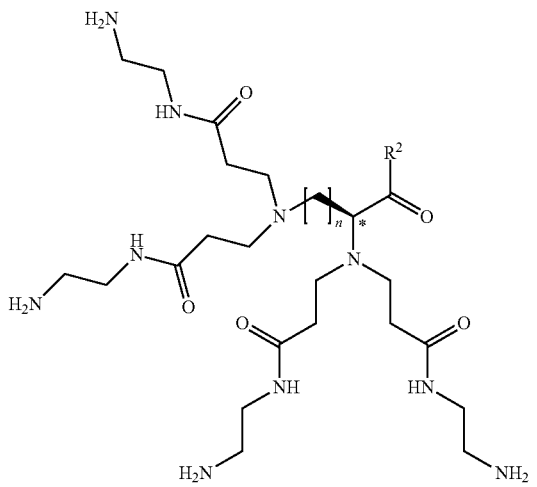

formula 4 wherein
n is an integer of from 1 to 4 inclusive
$R^2$ is a substituent independently selected from the group comprising an —$NH_2$ group, a substituent derived from an amide or $C_{1-6}$alkyl ester of a natural amino acid by removing a hydrogen atom from an amino group, a substituent derived from $C_{1-6}$alkyl ester of a linear or branched chain non-natural $C_{3-6}$aliphatic amino acid by removing a hydrogen atom from an amino group, as well as a substituent derived by removing a hydrogen atom from an amino group of a tryptamine, benzylamine optionally substituted by alkyl, phenylamine optionally substituted by nitro, aminopyridine, histamine, $C_5$-$C_{22}$aliphatic amine, aminocoumarin, cholesterylamine, or glucosamine molecule.

In particular, the compound is represented by the formula 4, wherein
$R^2$ is a substituent independently selected from the group comprising an —$NH_2$ group, a substituent derived from an amide or $C_{1-6}$alkyl ester of Phe, D-Phe, Tyr, D-Tyr, Ala, D-Ala, Gly, Ile, D-Ile, L and D-Trp by removing a hydrogen atom from an amino group, a substituent derived from $C_{1-6}$alkyl ester of a linear $C_{3-6}$aliphatic amino acid by removing a hydrogen atom from an amino group, as well as a substituent derived by removing a hydrogen atom from an amino group of a tryptamine, methylbenzylamine, benzylamine, nitrophenylamine, phenylamine, aminopyridine, histamine, $C_5$-$C_{22}$aliphatic amine, 7-aminocoumarin, cholesterylamine, or glucosamine molecule.

A process for the preparation of the dendrimeric compound comprising amino acids, according to the invention, is characterized by reacting an amino acid compound, in the D form, L form or a mixture of the D and L forms, of the formula 5

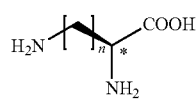

formula 5 wherein n is an integer of from 1 to 4 inclusive,
with $C_{1-6}$alkyl acrylate, optionally in the presence of a base, to yield a compound of the formula 6

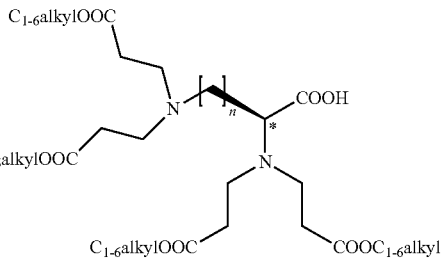

formula 6 followed by reacting the obtained compound of the formula 6, after optional acidification, with a primary organic amine or ammonia and the first coupling reagent to obtain an amide derivative of the formula 7

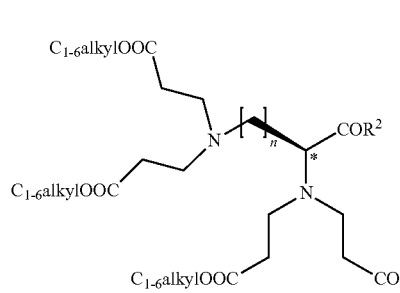

formula 7 which derivative of the formula 7 is subjected to aminolysis with ethylenediamine, to yield a branched core compound of the formula 3

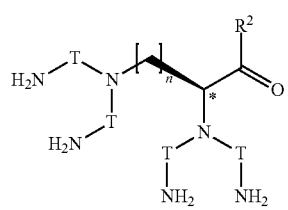

formula 3 followed by coupling the compound of the formula 3, wherein T is —(CH$_2$)$_2$CONH(CH$_2$)$_2$—, and R$^2$ is an —NH$_2$ group or a moiety derived from a primary organic amine molecule by removing a hydrogen atom from an amino group, with an amino acid and/or peptide, wherein at least one hydrogen atom of at least one amino group is optionally replaced by a protective group, in the presence of a second coupling reagent, to obtain a compound of the formula 1

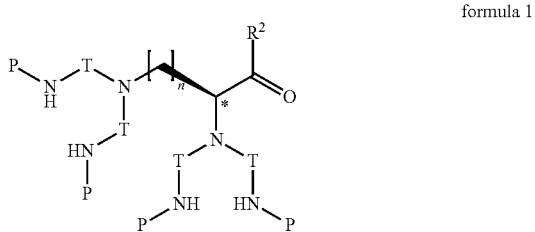

formula 1 wherein R$^2$ and T have meanings as disclosed above, and P is an amino acid and/or peptide moiety derived from an amino acid/peptide molecule by removing a hydroxy group from a carboxy group, in which amino acid/peptide moiety at least one hydrogen atom of at least one amino group is optionally replaced by a protective group,
optionally deprotecting the protected amino group and optionally converting into a pharmaceutically acceptable salt.

Preferably, the compound of the formula 2 is obtained,

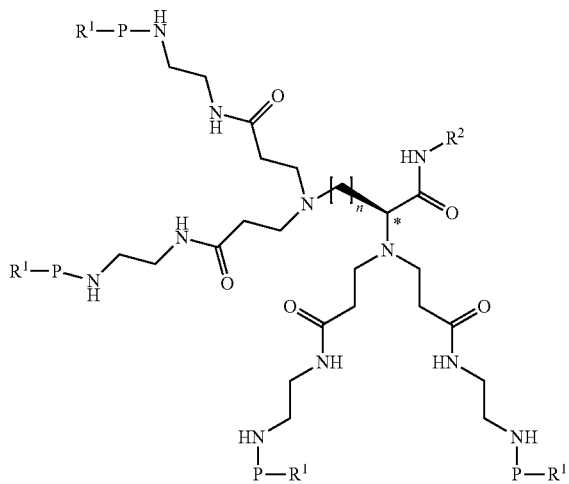

formula 2 wherein
P is a moiety derived from an amino acid molecule, in the D or L form, by removing a hydroxy group from a carboxy group of lysine, ornithine, arginine, 1,4-diaminobutyric acid (DAB), 1,3-diaminopropionic acid (DAP), at least one hydrogen atom of at least one amino group being optionally replaced by an R$^1$ substituent, R$^1$ is a substituent independently selected from the group comprising a hydrogen atom (H), benzyloxycarbonyl (Z), 2-chlorobenzyloxycarbonyl (2-Cl—Z), 2-bromobenzyloxycarbonyl (2-Br—Z), 2-iodobenzyloxycarbonyl (2-I—Z), t-butyloxycarbonyl (Boc), fatty alkylcarbonyl, fatty alkenylcarbonyl, dansyl (DNS), naphthylsulfonyl, 9-fluorenylmethoxycarbonyl (Fmoc), and moieties derived by removing a hydroxy group from a carboxy group of the following molecules: Lysine (Lys), D-Lysine (D-Lys), Z-Lys, Z-D-Lys, Lys-(ϵ-Z), D-Lys-(ϵ-Z), (2-Cl—Z)-Lys, (2-Cl—Z)-D-Lys, Lys-(ϵ-2-Cl—Z), D-Lys-(ϵ-2-Cl—Z), DNS-(Lys), Lys-(ϵ-DNS), or Z-Arg, Z-D-Arg, (2-Cl—Z)-Arg, (2-Cl—Z)-D-Arg, Lys-(Z)Lys[Lys-(Z)], D-Lys-(Z)Lys[D-Lys-(Z)], Lys-(Z)Orn[Lys-(Z)], D-Lys-(Z)Orn[D-Lys-(Z)], Z-Lys-Lys-[Z-Lys], Z-Lys-D-Lys-[Z-Lys], Z-D-Lys-Lys-[Z-D-Lys], Z-D-Lys-D-Lys-[Z-D-Lys], derivatives with analogous sequences wherein the starting lysine moiety is replaced by an ornithine moiety (Orn), derivatives with analogous sequences wherein the starting lysine moiety is replaced by a 2,4-diaminobutyric acid (DAB) moiety, derivatives with analogous sequences wherein the starting lysine moiety is replaced by a 2,4-diaminopropionic acid (DAP) moiety, Z-Arg-Lys[Z-Arg], Z-D-Arg-Lys[Z-D-Arg], Z-Arg-Orn[Z-Arg], Z-D-Arg-Orn[Z-D-Arg], Z-Arg-D-Lys-[Z-Arg], Z-D-Arg-D-Lys[Z-D-Arg], Z-Arg-D-Orn-[Z-Arg], Z-D-Arg-D-Orn[Z-D-Arg], (2-Cl—Z)-Arg-Lys[(2-Cl—Z)-Arg], (2-Cl—Z)-D-Arg-Lys[(2-Cl—Z)-D-Arg], (2-Cl—Z)-Arg-Orn[(2-Cl—Z)-Arg], (2-Cl—Z)-D-Arg-Orn[(2-Cl—Z)-D-Arg], (2-Cl—Z)-Arg-D-Lys-[(2-Cl—Z)-Arg], (2-Cl—Z)-D-Arg-D-Lys[(2-Cl—Z)-D-Arg], (2-Cl—Z)-Arg-D-Orn-[(2-Cl—Z)-Arg], (2Cl—Z)-D-Arg-D-Orn[(2-Cl—Z)-D-Arg], R$^2$ is a substituent independently selected from the group comprising an amino substituent, a substituent derived from an amide or C$_{1-6}$alkyl ester of Phe, D-Phe, Tyr, D-Tyr, Ala, D-Ala, Gly, Ile, D-Ile, L and D-Trp by removing a hydrogen atom from an amino group, a substituent derived from C$_{1-6}$alkyl ester of a linear C$_{3-6}$aliphatic amino acid by removing a hydrogen atom from an amino group, as well as a substituent derived by removing a hydrogen atom from an amino group of a tryptamine, methylbenzylamine, benzylamine, nitrophenylamine, phenylamine, aminopyridine, histamine, C$_5$-C$_{22}$aliphatic amine, 7-aminocoumarin, cholesterylamine, or glucosamine molecule.

Preferably, the first coupling reagent is a combination of NN'-dicyclohexylcarbodiimide (DCC) and N-hydroxysuccinimide, and the second coupling reagent is a combination of N,N'-dicyclohexylcarbodiimide (DCC) and N-hydroxysuccinimide.

In particular, the reaction of the amino acid compound of the formula 5 with C$_{1-6}$alkyl acrylate is carried out in the presence of an alcoholic solvent.

The reaction is preferably carried out at 60-90° C., especially at 65-80° C., for 24-48 hours.

The process for the preparation of the hyperbranched core compound, according to the invention is characterized by reacting an amino acid compound, in the D, L form or a mixture of the D and L forms, of the formula 5

formula 5 wherein n is an integer of from 1 to 4 inclusive, with $C_{1-6}$alkyl acrylate, optionally in the presence of a base, to yield a compound of the formula 6

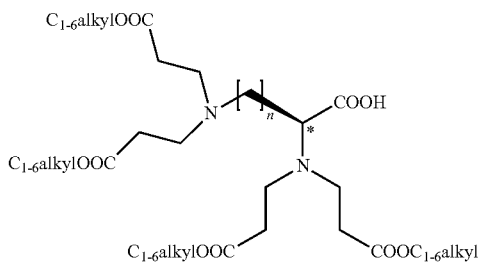

formula 6 followed by reacting the obtained compound of the formula 6, after optional acidification, with a primary organic amine or ammonia and a coupling reagent, to obtain an amide derivative of the formula 7

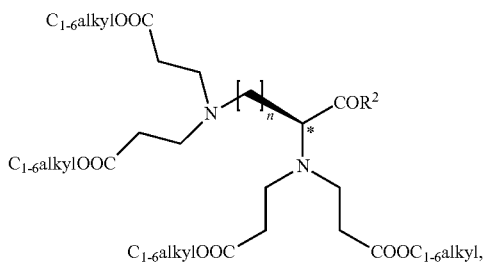

formula 7 which derivative of the formula 7 is subjected to aminolysis with ethylenediamine, to yield a branched core compound of the formula 3

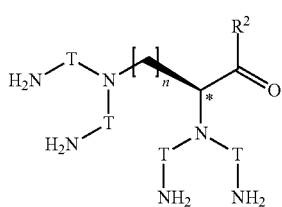

formula 3 wherein T is —$(CH_2)_2CONH(CH_2)_2$—, and $R^2$ is an —$NH_2$ group or a moiety derived from a primary organic amine molecule by removing a hydrogen atom from an amino group.

Preferably, the compound of the formula 4 is obtained formula 4 wherein n is an integer of from 1 to 4 inclusive $R^2$ is a substituent independently selected from the group comprising —$NH_2$, a substituent derived from an amide or $C_{1-6}$alkyl ester of Phe, D-Phe, Tyr, D-Tyr, Ala, D-Ala, Gly, Ile, D-Ile, L and D-Trp by removing a hydrogen atom from an amino group, a substituent derived from $C_{1-6}$alkyl ester of a linear $C_{3-6}$aliphatic amino acid by removing a hydrogen atom from an amino group, as well as a substituent derived by removing a hydrogen atom from an amino group of a tryptamine, methylbenzylamine, benzylamine, nitrophenylamine, phenylamine, aminopyridine, histamine, $C_5$-$C_{22}$aliphatic amine, 7-aminocoumarin, cholesterylamine, or glucosamine molecule.

In particular, the coupling reagent is a combination of N,N'-dicyclohexylcarbodiimide (DCC) and N-hydroxysuccinimide.

Especially, the reaction of the amino acid compound of the formula 5 with $C_{1-6}$ alkyl acrylate is carried out in the presence of an alcoholic solvent.

Preferably, the reaction is carried out at 60-90° C., especially at 65-80° C., for 24-48 hours.

The dendrimeric compound comprising amino acids, of the above-defined formula 1 according to the invention, is used for the manufacture of a medicament for pathogenic cell growth inhibition, in the prophylaxis or treatment of the human or animal body. Preferably, the dendrimeric compound is used for bacterial cell growth inhibition. Optionally, the dendrimeric compound is used for fungal cell growth inhibition. In particular, the dendrimeric compound is used for tumor cell growth inhibition.

Preferably, the dendrimeric compound of the formula 2 is used

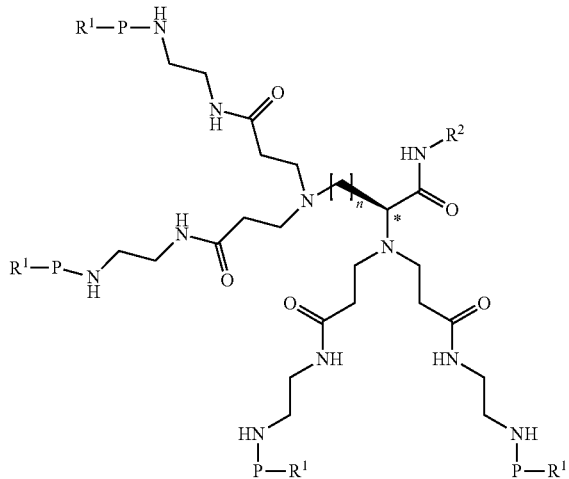

formula 2 wherein n is an integer of from 1 to 4 inclusive

P is a moiety derived from an amino acid molecule with two amino groups, by removing a hydroxy group from a carboxy group, at least one hydrogen atom of at least one amino group being optionally replaced by an $R^1$ substituent selected from the group comprising: fatty alkylcarbonyl, fatty alkenylcarbonyl, alkoxycarbonyl, arylalkoxy-carbonyl optionally substituted on the aryl by halo, arylsulfonyl substituted on the aryl by an alkylamino group, a moiety derived from an amino acid molecule with two amino groups, by removing a hydroxy group from a carboxy group, at least one hydrogen atom of at least one amino group being optionally replaced by a substituent selected from the group comprising fatty alkylcarbonyl, fatty alkenylcarbonyl, alkoxycarbonyl, arylalkoxycarbonyl optionally substituted on the aryl by halo, arylsulfonyl substituted on the aryl by an alkylamino group, or a moiety derived from a lysine, ornithine, 2,4-diaminobutyric acid or 2,3-diaminopropionic acid amino acid molecule, by removing a hydroxy group from a carboxy group;

$R^2$ is a substituent independently selected from the group comprising an amino substituent, a substituent derived from an amide or $C_{1-6}$alkyl ester of a natural amino acid by removing a hydrogen atom from an amino group, a substituent derived from $C_{1-6}$alkyl ester of a linear or branched chain non-natural $C_{3-6}$aliphatic amino acid by removing a hydrogen atom from an amino group, as well as a substituent derived by removing a hydrogen atom from an amino group of a tryptamine, benzylamine optionally substituted by alkyl, phenylamine optionally substituted by nitro, aminopyridine, histamine, $C_5$-$C_{22}$aliphatic amine, aminocoumarin, or cholesterylamine molecule.

In particular, the compound of the formula 2 is used in the form of a cationic salt with a pharmaceutically acceptable anion, especially in the form of the hydrochloride salt.

Preferably, the compound of the formula 2 is used, wherein:

n is an integer of from 1 to 4 inclusive,

P is a moiety derived from an amino acid molecule, in the D or L form, by removing a hydroxy group from a carboxy group of lysine, ornithine, arginine, 1,4-diaminobutyric acid (DAB), 1,3-diaminopropionic acid (DAP), at least one hydrogen atom of at least one amino group being optionally replaced by an $R^1$ substituent, $R^1$ is a substituent independently selected from the group comprising a hydrogen atom (H), benzyloxycarbonyl 2-chlorobenzyloxycarbonyl (2-Cl—Z), 2-bromobenzyloxycarbonyl (2-Br—Z), 2-iodobenzyloxycarbonyl (2-I—Z), t-butyloxycarbonyl (Boc), fatty alkylcarbonyl, fatty alkenylcarbonyl, dansyl (DNS), naphthylsulfonyl, 9-fluorenylmethoxycarbonyl (Fmoc), and moieties derived by removing a hydroxy group from a carboxy group of the following molecules: Lysine (Lys), D-Lysine (D-Lys), Z-Lys, Z-D-Lys, Lys-(ϵ-Z), D-Lys-(ϵ-Z), (2-Cl—Z)-Lys, (2-Cl—Z)-D-Lys, Lys-(ϵ-2-Cl—Z), D-Lys-(ϵ-2-Cl—Z), DNS-(Lys), Lys-(ϵ-DNS), or Z-Arg, Z-D-Arg, (2-Cl—Z)-Arg, (2-Cl—Z)-D-Arg, Lys-(Z)Lys[Lys-(Z)], D-Lys-(Z)Lys[D-Lys-(Z)], Lys-(Z)Orn[Lys-(Z)], D-Lys-(Z)Orn[D-Lys-(Z)], Z-Lys-Lys-[Z-Lys], Z-Lys-D-Lys-[Z-Lys], Z-D-Lys-Lys-[Z-D-Lys], Z-D-Lys-D-Lys-[Z-D-Lys], derivatives with analogous sequences wherein the starting lysine moiety is replaced by an ornithine moiety (Orn), derivatives with analogous sequences wherein the starting lysine moiety is replaced by a 2,4-diaminobutyric acid (DAB) moiety, derivatives with analogous sequences wherein the starting lysine moiety is replaced by a 2,4-diaminopropionic acid (DAP) moiety, Z-Arg-Lys[Z-Arg], Z-D-Arg-Lys[Z-D-Arg], Z-Arg-Orn [Z-Arg], Z-D-Arg-Orn[Z-D-Arg], Z-Arg-D-Lys-[Z-Arg], Z-D-Arg-D-Lys[Z-D-Arg], Z-Arg-D-Orn-[Z-Arg], Z-D-Arg-D-Orn[Z-D-Arg], (2-Cl—Z)-Arg-Lys[(2-Cl—Z)-Arg], (2-Cl—Z)-D-Arg-Lys[(2-Cl—Z)-D-Arg], (2-Cl—Z)-Arg-Orn[(2-Cl—Z)-Arg], (2-Cl—Z)-D-Arg-Orn[(2-Cl—Z)-D-Arg], (2-Cl—Z)-Arg-D-Lys-[(2-Cl—Z)-Arg], (2-Cl—Z)-D-Arg-D-Lys[(2-Cl—Z)-D-Arg], (2-Cl—Z)-Arg-D-Orn-[(2-Cl—Z)-Arg], (2Cl—Z)-D-Arg-D-Orn[(2-Cl—Z)-D-Arg], $R^2$ is a substituent independently selected from the group comprising an amino substituent, a substituent derived from an amide or $C_{1-6}$alkyl ester of Phe, D-Phe, Tyr, D-Tyr, Ala, D-Ala, Gly, Ile, D-Ile, L and D-Trp by removing a hydrogen atom from an amino group, a substituent derived from $C_{1-6}$alkyl ester of a linear $C_{3-6}$aliphatic amino acid by removing a hydrogen atom from an amino group, as well as a substituent derived by removing a hydrogen atom from an amino group of a tryptamine, methylbenzylamine, benzylamine, nitrophenylamine, phenylamine, aminopyridine, histamine, $C_5$-$C_{22}$aliphatic amine, 7-aminocoumarin, cholesterylamine, or glucosamine molecule.

In particular:

the compound of the formula 2, wherein n is 4, P—$R^1$ is $N^\alpha$-2-chlorobenzyloxycarbonyl-L-Arg and $R^2$ is a 3-aminopyridine moiety $C_5H_4N$—NH—, with the L-configuration on the chiral carbon atom linked to the —C(O)$R^2$ group, the compound of the formula 2, wherein n is 3, P—$R^1$ is $N^\epsilon$-2-chlorobenzyloxycarbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the faunula 2, wherein n is 3, P—$R^1$ is $N^\alpha$-2-chlorobenzyloxy-carbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 2, P—$R^1$ is $N^\alpha$-2-chlorobenzyloxy-carbonyl-L-Lys and $R^2$ is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 2, P—R¹ is N$^\alpha$-2-chlorobenzyloxy-carbonyl-L-Lys and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 3, P—R¹ is N$^\epsilon$-2-chlorobenzyloxy-carbonyl-L-Lys and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 1, P—R¹ is N$^\alpha$-2-chlorobenzyloxy-carbonyl-L-Lys and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 4, P—R¹ is N$^\alpha$-2-chlorobenzyloxy-carbonyl-L-Lys and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 4, P—R¹ is N$^\alpha$-benzyloxycarbonyl-L-Lys and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 4, P—R¹ is N$^\epsilon$-benzyloxycarbonyl-L-Lys and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 4, P—R¹ is N$^\alpha$-2-bromobenzyloxy-carbonyl-L-Lys and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 4, P—R¹ is N$^\alpha$-benzyloxycarbonyl-L-DAP and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 4, P—R¹ is N$^\alpha$-2-chlorobenzyloxy-carbonyl-L-Orn and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 3, P—R¹ is N$^\alpha$-2-chlorobenzyloxy-carbonyl-L-Lys and R² is a histamine moiety $C_3H_3N_2$—$CH_2$—$CH_2$—NH—, with the L-configuration on the chiral carbon atom linked to the —C(O)R² group, in a hydrochloride salt form, the compound of the formula 2, wherein n is 3, P—R¹ is N$^\epsilon$-2-chlorobenzyloxy-carbonyl-L-Lys and R² is a histamine moiety $C_3H_3N_2$—$CH_2$—$CH_2$—NH—, with the L-configuration on the chiral carbon atom linked to the —C(O)R² group, in a hydrochloride salt form, or the compound of the formula 2, wherein n is 3, P—R¹ is N$^\alpha$-2-chlorobenzyloxy-carbonyl-L-Lys and R² is a dodecylamine moiety $C_{12}H_{25}NH$—, with the L-configuration on the chiral carbon atom linked to the —C(O)R² group, in a hydrochloride salt form, is used.

The hyperbranched core compound of the above-defined formula 3 according to the invention, is used for the preparation of the macromolecular dendrimeric compounds comprising amino acids.

Preferably, a compound of the formula 4 is used

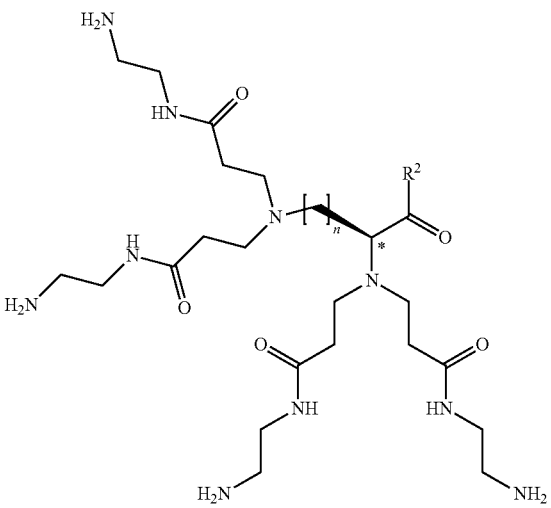

formula 4 wherein n is an integer of from 1 to 4 inclusive

R² is a substituent independently selected from the group comprising an —NH₂ group, a moiety derived from an amide or $C_{1-6}$alkyl ester of a natural amino acid by removing a hydrogen atom from an amino group, a substituent derived from $C_{1-6}$alkyl ester of a linear or branched chain non-natural $C_{3-6}$aliphatic amino acid, as well as a substituent derived by removing a hydrogen atom from an amino group of a tryptamine, benzylamine optionally substituted by alkyl, phenylamine optionally substituted by nitro, aminopyridine, histamine, $C_5$-$C_{22}$aliphatic amine, aminocoumarin, cholesterylamine, or glucosamine molecule.

In particular, the compound of the formula 4 is used, wherein

R² is a substituent independently selected from the group comprising an —NH₂ group, a substituent derived from an amide or $C_{1-6}$alkyl ester of Phe, D-Phe, Tyr, D-Tyr, Ala, D-Ala, Gly, Ile, D-Ile, L and D-Trp by removing a hydrogen atom from an amino group, a substituent derived from $C_{1-6}$alkyl ester of a linear $C_{3-6}$aliphatic amino acid by removing a hydrogen atom from an amino group, as well as a substituent derived by removing a hydrogen atom from an amino group of a tryptamine, methylbenzylamine, benzylamine, nitrophenylamine, phenylamine, aminopyridine, histamine, $C_5$-$C_{22}$aliphatic amine, aminocoumarin, cholesterylamine, or glucosamine molecule.

It was unexpectedly found that the central structure of a dendrimeric-compound can be modified in a manner to allow 3- or 4-fold branching of the compound structure in each reaction cycle. That unexpected effect was obtained by utilizing a sequence of reactions with Michael type addition reaction of lower alkyl acrylate and basic amino acids. As a consequence, uncomplicated and efficient synthetic procedure a novel hyperbranched core compound is obtained, which is an intermediate of the preparation of tetrabranched macromolecular dendrimeric compounds.

The dendrimeric compounds according to the invention exist in the form of a cationic salt with, e.g. an inorganic anion, especially in a hydrochloride salt form. Not wishing the invention to be bound by theory it is supposed that biological activities of the compounds are connected with a mechanism of electrostatic interactions between positively charged molecules of the dendrimer and negatively charged polar group of pathogenic cell, e.g. microbial cell or tumor cell biomembranes. The electrostatic effects influence electric equilibrium of the membrane, leading to disturbances in its structure and function. The dendrimeric compounds according to the invention, due to the novel structure of the core fragment, possess more labile structure which adapts to biological membranes and comprise greater number of diverse functional groups located on the dendrimer surface and in the tree. The dendrimeric compounds according to the invention, being derivatives of basic amino acids, are more compatible with natural biological systems (enzymes, proteins).

Molecules of dendrimeric compounds according to the invention are characterized by diverse conformational flexibility, amphiphilic structure, dimensions in the range of several nanometers and presence of a greater number of active groups in the dendrimeric structure. Thus it is possible to make the prepared dendrimeric compound more compatible with biological membranes or other receptor centers. A process for the preparation of the dendrimeric compound according to the invention allows to obtain a molecule of very high compaction of functional groups in a few reaction cycles.

The branched structure of the dendrimeric compounds according to the invention restricts the possibility of degradation of the compounds by proteolytic enzymes. Compounds according to the invention exhibit a broad spectrum of activities against Gram(+) bacteria, Gram(−) bacteria, fungi of the *C. albicans* genus, including multidrug resistant reference strains in each of the above groups, and against cells of the human MEW 155 melanoma.

In the context of the description and claims of the present invention, the term protective group denotes a group which protects an amino group. There is no specific limitation to the amino protecting group which could be used in the solutions according to the invention. Examples of typical protective groups can be found e.g. in the monograph "*Protective Groups in Organic Synthesis*" (Theodora W. Greene and Peter G. M. Wuts, $2^{nd}$ ed., 1991, John Wiley & Sons, Inc.). In the solution according to the invention, the term protective group embraces preferably such groups as: alkylcarbonyl such as fatty alkylcarbonyl, alkenylcarbonyl such as fatty alkenylcarbonyl, alkoxycarbonyl such as t-butyloxycarbonyl (Boc), arylalkoxycarbonyl such as benzyloxycarbonyl (Z), fluorenylmethoxycarbonyl (Fmoc), arylalkoxycarbonyl optionally substituted on the aryl by halo such as 2-chlorobenzyloxycarbonyl (2-Cl—Z), 2-bromobenzyloxycarbonyl (2-Br—Z), 2-iodobenzyloxycarbonyl (2-I—Z), arylsulfonyl such as naphthylsulfonyl, arylsulfonyl substituted on the aryl by an alkylamino group such as 5-(dimethylamino) naftaleno-1-sulfonyl (dansyl—DNS).

The dendrimeric compounds according to the invention and hyperbranched core compounds are obtained by a process according to the invention as illustrated on Scheme I.

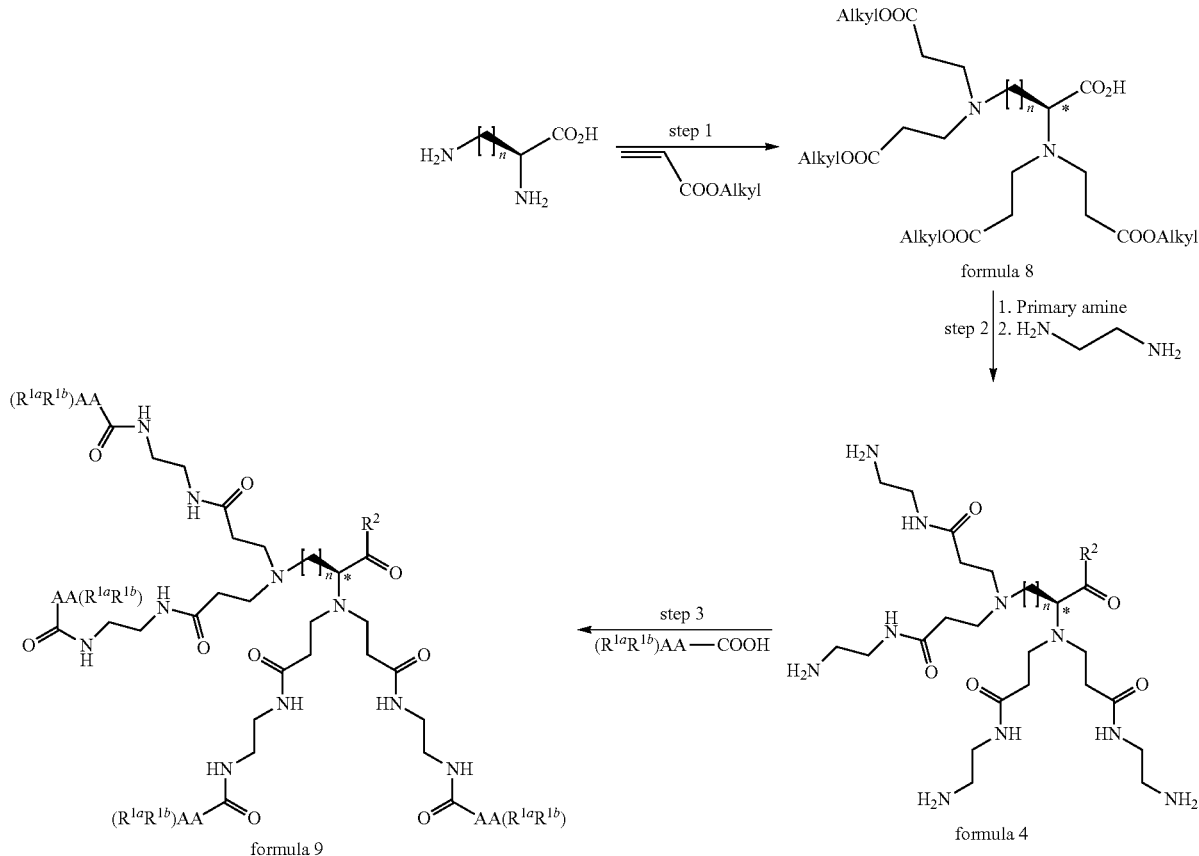

Scheme I formula 8 formula 9 formula 4

A process for the preparation of hyperbranched core compounds of the formula 4, wherein n is an integer of from 1 to 4 inclusive, according to the invention comprises a Michael addition reaction of alkyl acrylate, such as $C_{1-6}$alkyl acrylate, preferably linear acrylate and a basic amino acid, such as lysine (Lys), ornithine (Orn), 2,4-diaminobutyric acid (DAB), 2,3-diaminopropionic acid (DAP) (step 1), carried out in the presence of an alcoholic solvent, at 60-90° C., especially at 65-80° C., for 24-48 hours, optionally in the presence of a base, e.g. alkali metal hydroxide. The post-reaction mixture is optionally carefully neutralized by adding diluted mineral acid and the compounds of the formula 8 are isolated, purified and the free carboxy group is converted by coupling in the presence of a coupling reagent into an amide group, by reacting with an organic primary amine or ammonia ($R^2$ is an —$NHR^3$ substituent, wherein $R^3$ is H or an organic moiety derived from the organic amine). Preferable organic primary amines are amids or methyl esters of Phe, D-Phe, Tyr, D-Tyr, Ala, D-Ala, Gly, Ile, D-Ile, L and D-Trp amino acids; methyl esters of linear aliphatic amino acids containing from 3 do 6 carbon atoms, as well as tryptamine, methylbenzylamine, benzylamine, nitrophenylamine, phenylamine, 3-aminopyridine, histamine, saturated and unsaturated aliphatic amines with a $C_5$-$C_{22}$ chain, derivatives of coumarin, such as 7-aminocoumarin, glucosamine and cholesterylamine. In the second reaction of the step 2, aminolysis of ester groups with ethylenediamine is conducted.

In the step 3—in a branching reaction with the use of suitable amino acids, their derivatives protected by at least one protective $R^{1a}$, $R^{1b}$ group, or peptides, or peptides protected by at least one protective $R^{1a}$, $R^{1b}$ group, the dendrimeric compounds of the formula 9 are obtained.

A process for the preparation of the target dendrimeric compounds of the formula 9 (as well as of general formulae 1 and 2), according to the invention comprises coupling the branched core compound of the formula 4 with amino acids selected from the group comprising derivatives of lysine (Lys), ornithine (Orn), 2,4-diaminobutyric acid (DAB) and 2,3-diaminopropionic acid (DAP), N-terminally blocked by groups such as: benzyloxycarbonyl (Z) and/or 2-chlorobenzyloxycarbonyl (2-Cl—Z) and/or t-butyloxy-carbonyl (Boc), 2-bromobenzyloxycarbonyl (2-Br—Z), dansyl (DNS), naphthylsulfonyl, 9-fluorenylmethoxycarbonyl (Fmoc), or Z-Arg, Z-D-Arg, (2-Cl—Z)-Arg, (2-Cl—Z)-D-Arg, in the presence of a solvent and with the use of a coupling reagent such as a combination of N,N'-dicyclohexylcarbodiimide (DCC) and N-hydroxysuccinimide (HOSu), followed by purifying the obtained macromolecular dendrimeric compounds by chromatography, e.g. on a gel column containing Sephadex LH-20 (in MeOH), and optionally by preparative HPLC. The dendrimeric compounds (hexahydrochlorides) are optionally deprotected and converted into a cationic salt with an anion, which is preferably a pharmaceutically acceptable anion.

A synthesis of the dendrimeric compounds according to the invention, based on the novel hyperbranched core compounds according to the invention, is illustrated by the following examples.

General Process A (Step 1)

Preparation of Tetrakis(Methoxycarbonylethyl) Derivatives of Lys, Orn, DAB, DAP Amino Acids (Compounds of the Formula 8, Wherein Alkyl is Methyl)

The process according to the invention comprises carrying out the Michael addition reaction of methyl acrylate and corresponding Lys, Orn, DAB, DAP amino acids, followed by silica gel column purification of the obtained derivatives.

General Process B (Step 2)

Preparation of Tetrakis(Aminoethylaminocarbonylethyl) Amide Derivatives of Basic Lys, Orn, DAB, DAP Amino Acids In the compounds obtained in step 1 (by the process A) a carboxy group COOH is converted into —$COR^2$ derivatives by a reaction with compounds containing an —$NH_2$ group, comprising amides or methyl esters of Phe, D-Phe, Tyr, D-Tyr, Ala, D-Ala, Gly, Ile, D-Ile, L- and D-Trp; methyl esters of linear aliphatic amino acids containing from 3 to 6 carbon atoms, as well as tryptamine, methylbenzylamine, benzylamine, nitrophenylamine, phenylamine, 3-aminopyridine, histamine, a saturated and unsaturated aliphatic amine with a $C_5$-$C_{22}$ chain, derivatives of coumarin, glucosamine or cholesterylamine, by a coupling technique with DCC and HOBt. The amides obtained are converted into the compounds of the formula 4 by aminolysis with an ethylenediamine MeOH solution.

General Process C (Step 3)

Preparation of the Dendrimeric Compounds of the Formula 9

A process for the preparation of the target dendrimeric compounds of the formula 9, according to the invention, comprises coupling suitable branched core compounds of the formula 4 with amino acids selected from the group comprising derivatives of lysine (Lys), ornithine (Orn), 2,4-diaminobutyric acid (DAB) and 2,3-diaminopropionic acid (DAP), N-terminally blocked with group/groups selected from: benzyloxycarbonyl (Z) and/or 2-chlorobenzyloxycarbonyl (2-Cl—Z) and/or t-butyloxycarbonyl (Boc), 2-bromobenzyloxy-carbonyl (2-Br—Z), dansyl (DNS), naphthylsulfonyl, 9-fluorenylmethoxycarbonyl (Fmoc), or N-terminated with Z-Arg, Z-D-Arg, (2-Cl—Z)-Arg, (2-Cl—Z)-D-Arg, a moiety derived from glucosamine, a moiety derived from cholesterol, moieties derived from saturated and unsaturated fatty acids with a $C_5$-$C_{22}$ chain, by coupling in a solution with N,N'-dicyclohexylcarbodiimide (DCC) and N-hydroxysuccinimide (HOSu), followed by purifying the obtained macromolecular dendrimeric compounds by chromatography on a gel column containing Sephadex LH-20 (in MeOH), and optionally by preparative HPLC.

EXAMPLE 1

Synthesis of Tetrakis(Methoxycarbonylethyl) Derivatives of Lys, Orn, DAB, DAP Amino Acids (Scheme II)

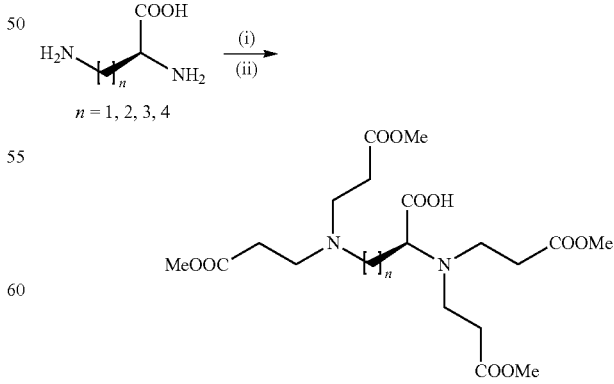

48-67%

(i) $CH_2$=CH—COOMe, NaOH, MeOH, 24 h, heating to the boil;
(ii) HCl/MeOH.

0.1 mol of a basic amino acid is suspended in 150 ml of MeOH, 4 g (0.1 mol) NaOH (0.2 mol for monohydrochlorides of Orn, L-DAB and L-DAP) in MeOH and 51.65 g (0.6 mol, 54 ml) of methyl acrylate is added. Reaction is carried out at the boiling point for 48 h, then cooled, the solvent evaporated (direct addition of HCl to the reaction mixture can cause polymerization of the remaining methyl acrylate), the oily residue is shaken with 300 ml of acetone and 100 ml of 1M HCl in MeOH (100 ml of 2M HCl for monohydrochlorides of Orn, L-DAB, L-DAP). The solution is filtered and evaporated to dryness. The residue is purified by column chromatography (SiO$_2$) with O:H (ethyl acetate:hexane) phase 8:2+5% MeOH, to yield tetrakis(methoxycarbonylethyl) derivatives as colorless or light yellow oils.

Compounds of Example 1

Tetrakis(Methoxycarbonylethyl) Derivatives of Basic Amino Acids

| Compound | Yield % | α[D] (±1)° |
|---|---|---|
| 2,6-bis-[bis-(3-methoxycarbonylethylamino)]-caproic acid (Lys derivative) (53) | 48.8[b] | −33.8[a] |
| 2,5-bis-[bis-(3-methoxycarbonylethylamino)]-valeric acid (Orn derivative) (54) | 67.7[b] | −32.6[a] |
| 2,5-bis-[bis-(3-methoxycarbonylethylamino)]-valeric acid (D,L-Orn derivative) (55) | 64.1[c] | — |
| 2,4-bis-[bis-(3-methoxycarbonylethylamino)]-butyric acid (L-DAB derivative) (56) | 44[b] | −32.9[a] |
| 2,3-bis-[bis-(3-methoxycarbonylethylamino)]-propionic acid (L-DAP derivative) (57) | 51.4[b] | −34.9[a] |

EXAMPLE 2

Synthesis of the Core Compound of the Formula 4, Wherein R² is the Tryptamine Moiety Scheme III

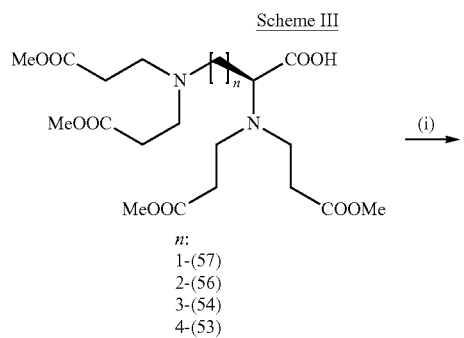

n:
1-(57)
2-(56)
3-(54)
4-(53)

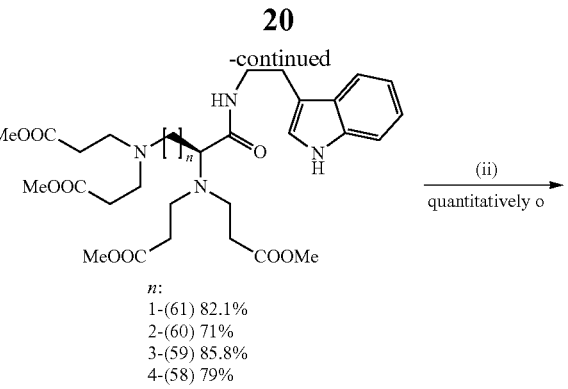

n:
1-(61) 82.1%
2-(60) 71%
3-(59) 85.8%
4-(58) 79%

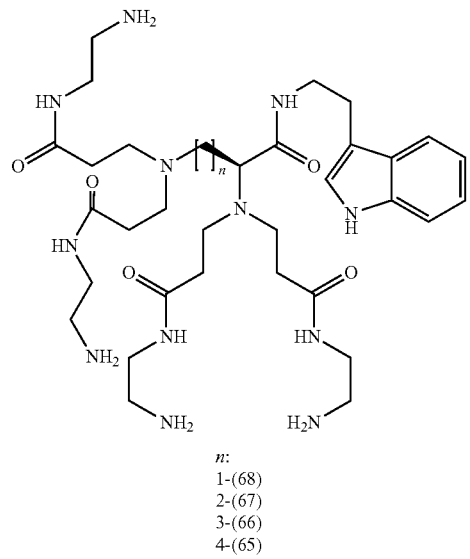

n:
1-(68)
2-(67)
3-(66)
4-(65)

(i) tryptamine, DCC, HOBt, DMF, 24 h;
(ii) ethylenediamine, MeOH, 5 days.

10 mmol of a methoxycarbonyl derivative of a basic amino acid with the L-configuration is dissolved in 30 ml of DMF, 3.2 g (20 mmol) of tryptamine, 1.54 g of HOBt (10 mmol, monohydrate) and 2.1 g of DCC (10.17 mmol) is added, and the mixture is stirred at the room temperature for 24 h. A DCU precipitate is then filtered off and the solvent evaporated. The oily residue is dissolved in 150 ml of ethyl acetate and washed with 150 ml of 10% aqueous Na$_2$CO$_3$, water, 1% citric acid (three times) and brine. The organic layer is dried (MgSO$_4$), filtered and evaporated to dryness. The residue is purified by column chromatography (SiO$_2$) with O:H phase 7:3+3% MeOH, to yield amide of tetrakis(methoxycarbonyl) derivative of lysine as a dark orange oil.

5 mmol of the amide is dissolved in 20 ml of MeOH and added very slowly dropwise to a mixture of 22.3 g (25 ml) of ethylenediamine and 50 ml of MeOH cooled to 0° C. The reaction is then stirred at the room temperature for 5 days, the solvents evaporated to dryness, 20 ml of butanol added to the residue and evaporated again. The operation is repeated three times more to remove traces of ethylenediamine. The prepared core compound, after being dried on a rotary evaporator for 6 h, is used directly for the synthesis of the dendrimeric compounds according to the invention, without further purification. Yield 99%.

EXAMPLE 3

Synthesis of the Compound of the Formula 9, Wherein AA is L-Lys, $R^{1a}$ is H, $R^{1b}$ is 2-Chlorobenzyloxycarbonyl, $R^2$ is a Tryptamine Moiety—Compound 98

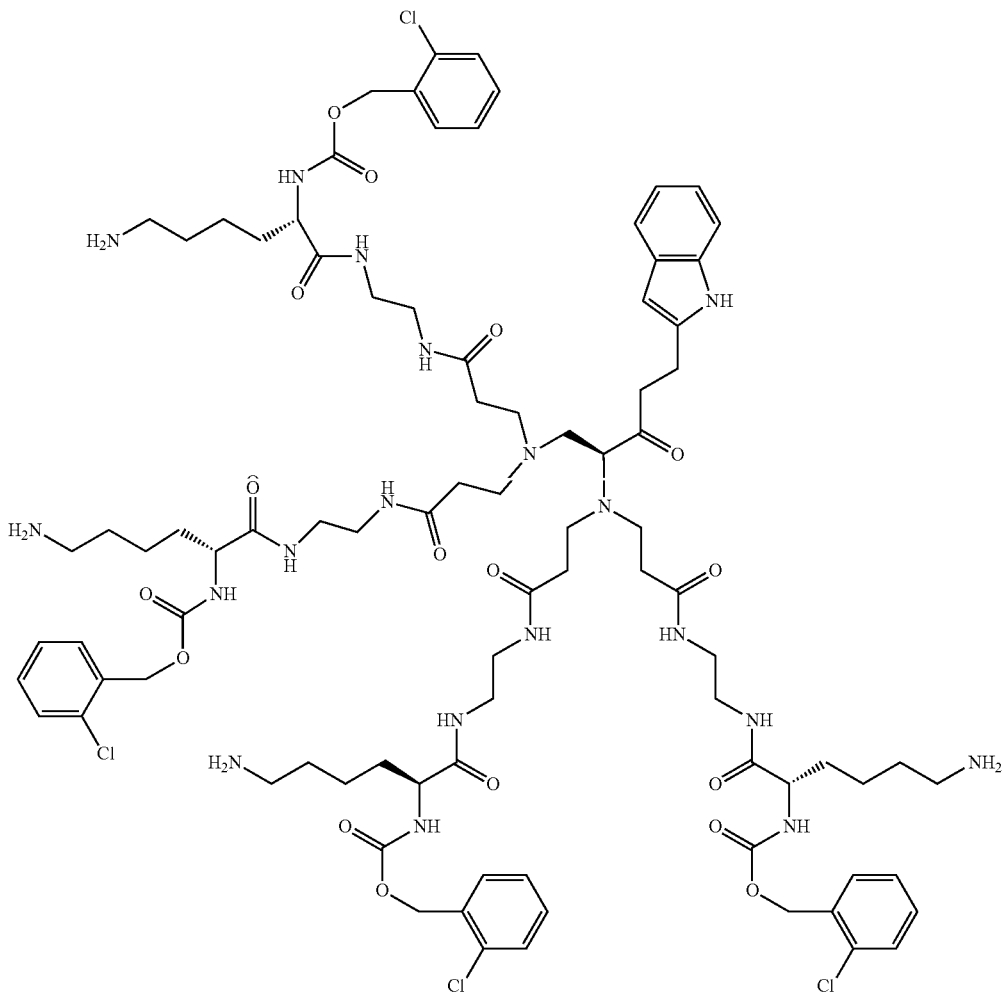

compound 98 formula 1.86 g (2.5 mmol) of a core compound is dissolved in 20 ml of DMF. To the obtained mixture, the solution of 4.56 g of (2-Cl—Z)-L-Lys(Boc) (11 mmol), 1.26 g of HOSu (11 mmol) and 2.31 g (11 mmol) of DCC in 20 ml THF is then added and stirred for 48 h at the room temperature. Afterwards, the mixture is filtered and the solvents evaporated. The residue is dissolved in 150 ml of EtOAc and washed with 10% $Na_2CO_3$ solution, 1% citric acid solution, dried over $MgSO_4$, filtered and evaporated. The raw dendrimeric compound is purified by molecular filtration on the Sephadex LH-20 packing in MeOH, to yield 3.66 g (62.8%) of the pure compound as a yellow amorphous foam. Dendrimer 98 is converted to its hexahydrochloride by deprotection of Boc-groups with TFA and replacing $CF_3COO^-$ anions with $Cl^-$ anions by the use of a saturated EtOAc solution of HCl, to yield slightly hygroscopic, brown amorphous powders.

Dendrimeric Compound 98

$C_{89}H_{126}O_{17}N_{20}Cl_4 \times 6HCl$, M=2108.6 g/mol (hexahydrochloride, monoisotopic weight of the non-protonated dendrimer—1886), brown amorphous foam.

MSLR (ESI, MeOH): 573.667 $(M-2-O—Z+3H^+)^{3+}$, 629.667 $(M+3H^+$ major signal$)^{3+}$, 647.667 $(M+2H^++Na^++MeOH)^3$, 944 $(M+2H^+)^{2+}$.

$^1$H NMR (400 MHz, DMSO, 298K) δ 1.3-1.7 (4 m, 24H, γ, δ, β$CH_2$ of lysines), 2.0-2.35 (m, 10H, $CH_2$CONH, β$CH_2$ of the core), 2.7-2.9 (2m, 8H, α, βN—$CH_2$—C), 3.0-3.4 (2bm, 29H, ε$CH_2$ of lysines, HN—$CH_2$—$CH_2$—NH of the core, $CH_2$—Ar trNH, —$CH_2$—NH trNH, αCH), 3.87 (m, 4H, αCH of lysines), 5.05-5.2 (4s, 8H, Ar—$CH_2$O), 6.95, 7.05, 7.12 (3m, 3H, $C_1$, $C_5$, $C_6$ trNH), 7.30-7.36 (m, 9H, $C_4$H, $C_5$H 2-Cl—Z, $C_7$ trNH), 7.40-7.51 (m, 8H, $C_3$H, $C_6$H 2-Cl—Z), 7.53 (m, 1H, $C_4$ trNH).

$^{13}$C NMR δ 22.3 (γC of lysines), 25.1 ($CH_2$—Ar trNH), 28.8 (δC of lysines), 31.3 (βC of lysines), 32.7, 34.9 (13, αCH$_2$CONH of the core), 38.0, 38.1 (εC of lysines), 39.1 (—CH$_2$—NH trNH), 39.9 (NHCH$_2$CH$_2$NH of the core), 47.0, 49.1 [α, βN—(CH$_2$)$_2$ of the core], 51.6 (βC of the core), 54.6 (αC of lysines), 61.4 (αC of the core), 62.5 (Ar—CH$_2$O), 111.0, 111.6, 117.8, 117.9, 120.5, 122.2 (C$_7$, C$_2$, C$_4$, C$_5$, C$_6$, C$_1$ trNH), 126.7 (C$_{5-2}$-Cl—Z), 127.1 (C$_3$ trNH), 128.8, 129.1, 129.2, 131.8, 134.0 (C$_6$, C$_4$, C$_3$, C$_2$, C$_1$ 2-Cl—Z), 136.1 (C$_8$ trNH), 155.2 (O—CO—NH), 171.3 (CH$_2$CONH of the core), 171.5 (CONH of the core), 171.6 (CONH of lysines).

TABLE 1

Compounds of the formula 9 (original numbering of compounds was preserved, R$^{1a}$ and R$^{1b}$ are substituents on a nitrogen atom of an N$^α$ amino group and a nitrogen atom of the peptide or amino acid terminal amino group, respectively, N$^ε$ for lysine)

| No. | n | AA | R$^{1a}$ | R$^{1b}$ | R$^2$ | ESI MS* spectrum |
|---|---|---|---|---|---|---|
| 86 | 4 | L-Arg | 2-Cl—Z | H | 3-AMP | C$_{92}$H$_{132}$O$_{17}$N$_{28}$Cl$_4$, M = 2044.0 g/mol (monoisotopic weight of the dendrimer - 2040); MSLR (ESI, MeOH): 1021 (M + 2H$^+$)$^{2+}$, 1032 (M + H$^+$ + Na$^+$)$^{2+}$, 2041 (M + H$^+$). |
| 92 | (D, L) 3 | L-Lys | H | 2-Cl—Z | TrNH | C$_{86}$H$_{124}$O$_{17}$N$_{20}$Cl$_4$ × 7HCl, M = 2107.0 g/mol (monoisotopic weight of the non-protonated dendrimer - 1848); MSLR (ESI, MeOH): 617 (M + 3H$^+$, major signal)$^{3+}$, 635 (M + 2H$^+$ + Na$^+$ + MeOH)$^{3+}$, 925 (M + 2H$^+$)$^{2+}$, 952 (M + H$^+$ + Na$^+$ + MeOH)$^{2+}$ |
| 93 | (D, L) 3 | L-Lys | 2-Cl—Z | H | TrNH | C$_{86}$H$_{124}$O$_{17}$N$_{20}$Cl$_4$ × 7HCl, M = 2107.0 g/mol (monoisotopic weight of the non-protonated dendrimer - 1848); MSLR (ESI, MeOH): 617 (M + 3H$^+$ major signal)$^{3+}$, 925 (M + 2H$^+$)$^{2+}$ |
| 94 | 2 | L-Lys | 2-Cl—Z | H | TrNH | C$_{90}$H$_{128}$O$_{17}$N$_{20}$Cl$_4$ × 6HCl, M = 2122.6 g/mol (monoisotopic weight of the non-protonated dendrimer - 1900); MSLR (ESI, MeOH): 634.334 (M + 3H$^+$)$^{3+}$, 649 (M + H$^+$ + 2Na$^+$ major signal)$^{3+}$, 672.334 (M + 2Na$^+$ + K$^+$ + MeOH)$^{3+}$, 951 (M + 2H$^+$)$^{2+}$, 973 (M + 2Na$^+$)$^{2+}$. |
| 95 | 2 | L-Lys | H | 2-Cl—Z | TrNH | C$_{90}$H$_{128}$O$_{17}$N$_{20}$Cl$_4$ × 6HCl, M = 2122.6 g/mol (monoisotopic weight of the non-protonated dendrimer - 1900), brown foam). MSLR (ESI, MeOH): 634.334 (M + 3H$^+$)$^{3+}$, 649 (M + H$^+$ + 2Na$^+$ major signal)$^{3+}$, 672.334 (M + 2Na$^+$ + K$^+$ + MeOH)$^{3+}$, 973 (M + 2Na$^+$)$^{2+}$. |
| 96 | 3 | L-Lys | 2-Cl—Z | H | TrNH | C$_{91}$H$_{130}$O$_{17}$N$_{20}$Cl$_4$ × 6HCl, M = 2136.7 g/mol (monoisotopic weight of the non-protonated dendrimer - 1914); MSLR (ESI, MeOH): 639 (M + 3H$^4$)$^{3+}$, 653.667 (M + H$^+$ + 2Na$^+$ major signal)$^3$, 958 (M + 2H$^+$)$^{2+}$, 980 (M + 2Na$^+$)$^{2+}$. |
| 98 | 1 | L-Lys | 2-Cl—Z | H | TrNH | C$_{89}$H$_{126}$O$_{17}$N$_{20}$Cl$_4$ × 6HCl, M = 2108.6 g/mol (monoisotopic weight of the non-protonated dendrimer - 1886); MSLR (ESI, MeOH): 573.667 (M − 2-Cl—Z + 3H$^+$)$^{3+}$, 629.667 (M + 3H$^+$ major signal)$^{3+}$, 647.667 (M + 2H$^+$ + Na$^+$ + MeOH)$^3$, 944 (M + 2H$^+$)$^{2+}$. |
| 100 | 4 | L-Lys | 2-Cl—Z | H | TrNH | C$_{92}$H$_{132}$O$_{17}$N$_{20}$Cl$_4$ × 6HCl, M = 2150.7 g/mol (monoisotopic weight of the non-protonated dendrimer - 1928); MSLR (ESI, MeOH): 643.667 (M + 3H$^+$ major signal)$^{3+}$, 661.667 (M + 2H$^+$ + Na$^+$ + MeOH)$^{3+}$, 679.667 (M + H$^+$ + 2Na$^+$ + 2MeOH)$^{3+}$, 965 (M + 2H$^+$)$^{2+}$, 995 (M + Na$^+$ + K$^+$)$^{2+}$. |
| 102 | 4 | L-Lys | Z | H | TrNH | C$_{92}$H$_{136}$O$_{17}$N$_{20}$ × 6HCl, M = 2012.9 g/mol (monoisotopic weight of the non-protonated dendrimer - 1792); MSLR (ESI, MeOH): 509 (M − 2 × Z + 3H$^+$)$^{3+}$, 553.667 (M − Z + 3H$^+$)$^{3+}$, 598.334 (M + 3H$^+$, major signal)$^{3+}$, 616.334 (M + 2H$^+$ + Na$^+$ + MeOH)$^{3+}$, 897 (M + 2H$^+$)$^{2+}$. |
| 103 | 4 | L-Lys | H | Z | TrNH | C$_{92}$H$_{136}$O$_{17}$N$_{20}$ × 6HCl, M = 2012.9 g/mol (monoisotopic weight of the non-protonated dendrimer - 1792); MSLR (ESI, MeOH): 509 (M − 2 × Z + 3H$^4$)$^{3+}$, 553.667 (M − Z + 3H$^+$)$^{3+}$, 598.334 (M + 3H$^+$, major signal)$^{3+}$, 616.334 (M + 2H$^+$ + Na$^+$ + MeOH)$^{3+}$, 897 (M + 2H$^+$)$^{2+}$. |
| 104 | 4 | L-Lys | 2-Br—Z | H | TrNH | C$_{92}$H$_{132}$O$_{17}$N$_{20}$Br$_4$ × 6HCl, M = 2328.5 g/mol (monoisotopic weight of the non-protonated dendrimer - 2104); MSLR (ESI, MeOH): 589.667 (M − 2 × 2-Br—Z + 2H$^+$ + Na$^+$ + 2 × MeOH)$^{3+}$, 617 (M − 2 × 2-Br—Z + 2H$^+$ + 169, where 169 - 2-bromobenzyl cation C$_7$H$_6$Br)$^{3+}$, 642.334 (M − 2-Br—Z + 3H$^+$ + MeOH)$^{3+}$, 702.334 (M + 3H$^+$, major signal)$^{3+}$, 720.334 (M + 2H$^+$ + Na$^+$ + MeOH)$^{3+}$, 1053 (M + 2H$^+$)$^{2+}$. |

TABLE 1-continued

Compounds of the formula 9 (original numbering of compounds was preserved, $R^{1a}$ and $R^{1b}$ are substituents on a nitrogen atom of an $N^{\alpha}$ amino group and a nitrogen atom of the peptide or amino acid terminal amino group, respectively, $N^{\epsilon}$ for lysine)

| No. | n | AA | $R^{1a}$ | $R^{1b}$ | $R^2$ | ESI MS* spectrum |
|---|---|---|---|---|---|---|
| 105 | 4 | L-DAP | Z | H | TrNH | $C_{80}H_{112}O_{17}N_{20}$ × 6HCl, M = 2160.2 g/mol (monoisotopic weight of the non-protonated dendrimer - 1624); MSLR (ESI, MeOH): 542.334 $(M + 3H^+$, major signal$)^{3+}$, 560.334 $(M + 2H^+ + Na^+ + MeOH)^{3+}$, 813 $(M + 2H^+)^{2+}$. |
| 106 | 4 | L-Orn | 2-Cl—Z | H | TrNH | $C_{88}H_{124}O_{17}N_{20}Cl_4$ × 6HCl, M = 2094.6 g/mol (monoisotopic weight of the non-protonated dendrimer - 1872); MSLR (ESI, MeOH): 625 (M + 3 major signal)$^{3+}$, 643 $(M + 2H^+ + Na^+ + MeOH)^{3+}$, 937 $(M + 2H^+)^{2+}$. |
| 107 | 3 | L-Lys | 2-Cl—Z | H | HiNH | $C_{86}H_{127}O_{17}N_{21}Cl_4$ × 7HCl, M = 2124.1 g/mol (monoisotopic weight of the non-protonated dendrimer - 1865); MSLR (ESI, MeOH): 622.667 $(M + 3H^+$, practically a sole signal$)^{3+}$. |
| 108 | 3 | L-Lys | H | 2-Cl—Z | HiNH | $C_{86}H_{127}O_{17}N_{21}Cl_4$ × 7HCl, M = 2124.1 g/mol (monoisotopic weight of a non-protonated dendrimer - 1865); MSLR (ESI, MeOH): 566.667 (M − 2-Cl—Z + 3H$^+$)$^{3+}$, 622.667 $(M + 3H^+$, major signal$)^{3+}$, 933.5 $(M + 2H^+)^{2+}$. |
| 109 | 3 | L-Lys | 2-Cl—Z | H | DDA | $C_{93}H_{145}O_{17}N_{19}Cl_4$ × 6HCl, M = 2161.8 g/mol (monoisotopic weight of a non-protonated dendrimer - 1939); MSLR (ESI, MeOH): 647.334 $(M + 3H^+$, major signal$)^{3+}$, 970.5 $(M + 2H^+)^{2+}$. |

Abbreviations used in Table 1:
3-AMP—3-aminopyridine moiety, $C_5H_4N$—NH—
TrNH—tryptamine moiety, $C_8H_6N$—$CH_2$—$CH_2$—NH—
HiNH—histamine moiety, $C_3H_3N_2$—$CH_2$—$CH_2$—NH—
DDA—dodecylamine moiety, $C_{12}H_{25}NH$—

EXAMPLE 4

Antimicrobial Activity In Vitro Assay

Values of a minimal inhibitory concentration—MIC of compounds according to the invention for bacterial strains were assayed by a standard method of microdilutions on a liquid substrate (Clinical and Laboratory Standards Institute 2007. Methods for Dilution Antimicrobial Susceptibility Tests for Bacteria That Grow Aerobically. Approved Standard—Seventh Edition. M7-A7. Clinical and Laboratory Standards Institute, Wayne, Pa., USA).

A series of double dilutions of the tested compounds in DMSO was prepared. They were then diluted 95× in CAMHB (Cation Adjusted Mueller—Hinton Broth).

Bacteria were cultured for 24 h at 35° C. under aerobic conditions on a solid TSA (Triptic Soy Agar) medium. A volume of a proper test was 0.1 ml and was composed of: 0.005 ml of a saline suspension of bacteria at a density of $10^7$ CFU/ml (final bacteria amount of 5×10$^5$/ml) and 0.095 ml of a tested compound CAMHB solution. Final concentrations of compounds in the proper test were (µg/ml): 128, 64, 32, 16, 8, 4, 2, 1.

A blind test was comprised of: 0.005 ml of CAMHB medium and 0.095 ml of a tested compound CAMHB solution.

A control was comprised of: 0.005 ml of a saline suspension of bacteria at a density of $10^7$ CFU/ml (final bacteria amount of 5×10$^5$/ml) and 0.095 ml of CAMHB.

Titration plates with a, b, d strains were incubated for 18 h at 35° C. under aerobic conditions, and the c strain was incubated for 18 h at 33° C. under aerobic conditions.

Tables 2-4 show results of antibacterial and antifungal activities in vitro of the dendrimeric compounds according to the invention, against microbial strains of:
a) *Pseudomonas aeruginosa* ATCC 27853,
b) *Staphylococus aureus* subsp. *aureus* ATCC 25923,
c) *Staphylococus aureus* subsp. *aureus* ATCC 43300,
d) *Escherichia coli* ATCC 25922
e) *C. albicans* ATCC 10231.

TABLE 2

Minimal inhibitory concentration (MIC) values assayed for the dendrimeric compounds 94-101 (2 series of compounds with differences in the inner core length only: from L-DAP - $C_3$ to L-Lys - $C_6$; $N^{\alpha}$-2-Cl—Z and $N^{\epsilon}$-2-Cl—Z series differ only in distribution of aromatic protective moieties at lysine branches of a dendrimer)

| | MIC values in µM/L | | | | | | | |
|---|---|---|---|---|---|---|---|---|
| | $N^{\alpha}$-2-Cl—Z series | | | | $N^{\epsilon}$-2-Cl—Z Series | | | |
| Strain tested | 98 (DAP) | 94 (DAB) | 96 (Orn) | 100 (Lys) | 99 (DAP) | 95 (DAB) | 97 (Orn) | 101 (Lys) |
| S. aureus ATCC 25923 | 0.95 | 0.94 | 1.87 | 0.93 | 0.6 | 1.88 | 0.93 | 0.93 |
| S. aureus ATTC 43300 | 8.06 | 10.12 | 12.1 | 5.81 | 3.32 | 32 | 20.4 | 10.0 |

TABLE 2-continued

Minimal inhibitory concentration (MIC) values assayed for the dendrimeric compounds 94-101 (2 series of compounds with differences in the inner core length only: from L-DAP - $C_3$ to L-Lys - $C_6$; $N^\alpha$-2-Cl—Z and $N^\epsilon$-2-Cl—Z series differ only in distribution of aromatic protective moieties at lysine branches of a dendrimer)

| | MIC values in µM/L | | | | | | | |
|---|---|---|---|---|---|---|---|---|
| | $N^\alpha$-2-Cl—Z series | | | | $N^\epsilon$-2-Cl—Z Series | | | |
| Strain tested | 98 (DAP) | 94 (DAB) | 96 (Orn) | 100 (Lys) | 99 (DAP) | 95 (DAB) | 97 (Orn) | 101 (Lys) |
| *E. coli* ATTC 25922 | 12.3 | 12.2 | 12.1 | 3.71 | 7.0 | 32 | 7.9 | 12.0 |
| *P. aeruginosa* ATTC 27853 | 52 | 70 | 51 | 41 | 52 | 51 | 60 | 51 |

TABLE 3

Minimal inhibitory concentration (MIC) values assayed for the dendrimeric compounds 100-106 and 86

| | MIC values in µM/L | | | | | | | |
|---|---|---|---|---|---|---|---|---|
| Strain tested | 100 (2-Cl—Z)-Lys | 101 Lys(2-Cl—Z) | 102 Z-Lys | 103 Lys(Z) | 104 (2-Br—Z)-Lys | 105 Z-L-DAP | 106 (2-Cl—Z)-Orn | 86 (2-Cl—Z)-Arg |
| *S. aureus* ATCC 25923 | 0.93 | 0.93 | 17.3 | 12.9 | 3.43 | 38 | 3.82 | 17.1 |
| *S. aureus* ATTC 43300 | 5.81 | 10.0 | 149 | 74 | 30 | 81 | 25 | 3.91 |
| *E. coli* ATTC 25922 | 3.71 | 12.0 | 149 | 111 | 30 | 81 | 16.7 | 17.1 |
| *P. aeruginosa* ATTC 27853 | 41 | 51 | 149 | 149 | 64 | 81 | 71 | 73 |
| *C. albicans* ATCC 10231 | nt | nt | nt | nt | nt | 81 | nt | 73 |

(nt—not tested)

TABLE 4

Minimal inhibitory concentration (MIC) values assayed for the dendrimeric compounds 92, 93, 96, 97, and 107-110 (dendrimers based on a constant length core, with the same branching element, but differing in the kind of a core C-terminal blocking amine).

| | MIC values in µM/L | | | | | | | |
|---|---|---|---|---|---|---|---|---|
| | $N^\alpha$-2-Cl—Z series | | | | $N^\epsilon$-2-Cl—Z series | | | |
| Strain tested | 93 (3-AP) | 96 (trNH) | 107 (hiN) | 109 (dda) | 92 (3-AP) | 97 (trNH) | 108 (hiN) | 110 (dda) |
| *S. aureus* ATCC 25923 | 2.85 | 1.87 | 24.7 | 1.85 | 16.6 | 0.93 | 51 | 3.7 |
| *S. aureus* ATTC 43300 | 439 | 12.1 | 141 | 0.46 | 142 | 20.4 | 16.4 | 1.85 |
| *E. coli* ATTC 25922 | 439 | 12.1 | 141 | 1.85 | 142 | 7.9 | 211 | 7.9 |
| *P. aeruginosa* ATTC 27853 | 439 | 51 | 141 | 7.8 | 142 | 60 | 211 | 32 |
| *C. albicans* ATCC 10231 | nt | nt | nt | 69 | nt | nt | nt | 139 |

Abbreviations used in the table:
(3-AP)—3-aminopyridine;
(trNH)—tryptamine,
(hiN)—histamine,
(dda)—dodecylamine
(nt—not tested)

EXAMPLE 5

Test of Dendrimeric Peptide Influence on Numbers of Live Human MWE155 Melanoma Cells Human melanoma cells (MEW 155) received from Institute of Oncology were inoculated on Petri dishes (Ø3 cm, Nunc) to the number of about 75 000, suspended in 3 ml of Eagle medium+10% FBS+antibiotics. Immediately after the inoculation, solutions of tested substances were added to the cells (a substance +20 ml PBS) at 0.5 ml per dish. After culturing for 3 days, numbers of cells (all, dead and alive) at each dish were determined with NucleoCounter apparatus (Chemometec). Table 5 shows percentages of live cells remaining on a dish after a dendrimer in a given concentration was added.

TABLE 5

Influence of the dendrimeric compounds according to the invention on a survival rate of human melanoma cells (MEW 155) in the in vitro assays

| Compound No. | Concentration ($\mu$Mol dm$^{-3}$) | Live cells (%) |
| --- | --- | --- |
| 92 | 7.14 | 97.7 |
| 93 | 13.65 | 95.8 |
| 94 | 12.13 | 88.4 |
| 96 | 33.6 | 11.6 |
| 98 | 4.3 | 97.7 |
| 100 | 25.7 | 0 |
| 102 | 13.6 | 98.5 |
| 103 | 15.0 | 96.5 |
| 104 | 21.4 | 73.6 |
| 105 | 10.0 | 97.7 |
| 106 | 10.0 | 87.7 |
| 107 | 47.1 | 91.1 |
| 108 | 42.1 | 94.9 |
| 109 | 25.7 | 1.5 |

The dendrimeric compounds according to the invention can have preventive or therapeutic use in humans or animals, e.g. for the manufacture of medicaments for the treatment of infections caused by bacteria or fungi, for the treatment of some forms of tumors, as well as for the preparation of compositions for maintaining sterile environment.

The invention claimed is:

1. Dendrimeric compounds comprising amino acids, of the formula 1

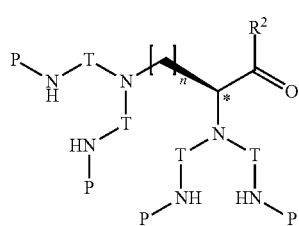

formula 1 comprising a branched core with four -T-NH— branches, wherein n is an integer from 1 to 4 inclusive, wherein T is an alkylidene group —(CH$_2$)$_2$CONH(CH$_2$)$_2$—, and one R$^2$ branch, wherein R$^2$ is an —NH$_2$ group, or a moiety derived from a primary organic amine molecule, by removing a hydrogen atom from an amino group, and comprising at least four P terminal fragments, wherein P is an amino acid and/or peptide moiety derived from an amino acid/peptide molecule by removing a hydroxy group from a carboxy group, said amino acid/peptide moiety having at least one hydrogen atom at least one amino group optionally replaced by a protective group.

2. Compounds according to claim 1, of the formula 2

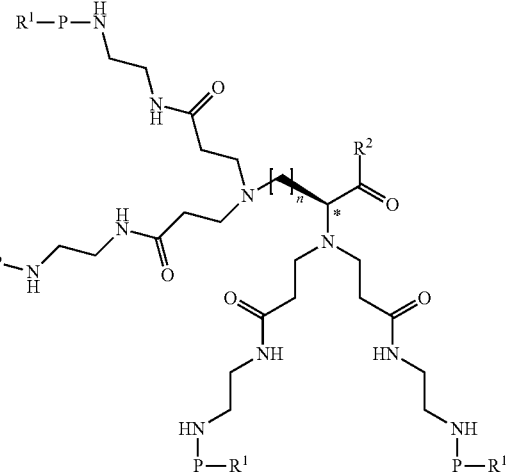

formula 2 wherein n is an integer of from 1 to 4 inclusive

P is a moiety derived from an amino acid molecule with two amino groups, by removing a hydroxy group from a carboxy group, at least one hydrogen atom of at least one amino group being optionally replaced by an R$^1$ substituent selected from the group comprising: fatty alkylcarbonyl, fatty alkenylcarbonyl, alkoxycarbonyl, arylalkoxycarbonyl optionally substituted on the aryl by halo, arylsulfonyl substituted on the aryl by an alkylamino group, a moiety derived from an amino acid molecule with two amino groups, by removing a hydroxy group from a carboxy group, at least one hydrogen atom of at least one amino group being optionally replaced by a substituent selected from the group comprising fatty alkylcarbonyl, fatty alkenylcarbonyl, alkoxycarbonyl, arylalkoxycarbonyl optionally substituted on the aryl by halo, arylsulfonyl substituted on the aryl by an alkylamino group, or a moiety derived from a lysine, ornithine, 2,4-diaminobutyric acid or 2,3-diaminopropionic acid amino acid molecule, by removing a hydroxy group from a carboxy group;

R$^2$ is a substituent independently selected from the group comprising an amino substituent, a substituent derived from an amide or C$_{1-6}$alkyl ester of a natural amino acid by removing a hydrogen atom from an amino group, a substituent derived from C$_{1-6}$alkyl ester of a linear or branched chain non-natural C$_{3-6}$aliphatic amino acid by removing a hydrogen atom from an amino group, as well as a substituent derived by removing a hydrogen atom from an amino group of a tryptamine, benzylamine optionally substituted by alkyl, phenylamine optionally substituted by nitro, aminopyridine, histamine, C$_5$-C$_{22}$aliphatic amine, aminocoumarin, or cholesterylamine molecule.

3. Compounds according to claim 2, characterized in that the compounds are in the form of a cationic salt with a pharmaceutically acceptable anion.

4. Compounds according to claim 3, characterized in that the compounds are in the form of hydrochloride salts.

5. Compounds according to claim 2, characterized in that:
n is an integer of from 1 to 4 inclusive, P is a moiety derived from an amino acid molecule, in the D or L form, by removing a hydroxy group from a carboxy group of lysine, ornithine, arginine, 1,4-diaminobutyric acid (DAB), 1,3-diaminopropionic acid (DAP), at least one hydrogen atom of at least one amino group being optionally replaced by an $R^1$ substituent, $R^1$ is a substituent independently selected from the group comprising a hydrogen atom (H), benzyloxycarbonyl (Z), 2-chlorobenzyloxycarbonyl (2-Cl-Z), 2-bromobenzyloxycarbonyl (2-Br-Z), 2-iodobenzyloxycarbonyl (2-I-Z), t-butyloxycarbonyl (Boc), fatty alkylcarbonyl, fatty alkenylcarbonyl, dansyl (DNS), naphthylsulfonyl, 9-fluorenylmethoxycarbonyl (Fmoc), and moieties derived by removing a hydroxy group from a carboxy group of the following molecules: Lysine (Lys), D-Lysine (D-Lys), Z-Lys, Z-D-Lys, Lys-(ε-Z), D-Lys-(ε-Z), (2-Cl-Z)-Lys, (2-Cl-Z)-D-Lys, Lys-(ε-2-Cl-Z), D-Lys-(ε-2-Cl-Z), DNS-(Lys), Lys-(ε-DNS), or Z-Arg, Z-D-Arg, (2-Cl-Z)-Arg, (2-Cl-Z)-D-Arg, Lys-(Z)Lys [Lys-(Z)], D-Lys-(Z)Lys[D-Lys-(Z)], Lys-(Z)Orn[Lys-(Z)], D-Lys-(Z)Orn[D-Lys-(Z)], Z-Lys-Lys-[Z-Lys], Z-Lys-D-Lys-[Z-Lys], Z-D-Lys-Lys-[Z-D-Lys], Z-D-Lys-D-Lys-[Z-D-Lys], derivatives with analogous sequences, wherein the starting lysine moiety is replaced by an ornithine moiety (Orn), derivatives with analogous sequences, wherein the starting lysine moiety is replaced by a 2,4-diaminobutyric acid (DAB) moiety, derivatives with analogous sequences, wherein the starting lysine moiety is replaced by a 2,4-diaminopropionic acid (DAP) moiety, Z-Arg-Lys[Z-Arg], Z-D-Arg-Lys[Z-D-Arg], Z-Arg-Orn [Z-Arg], Z-D-Arg-Orn[Z-D-Arg], Z-Arg-D-Lys-[Z-Arg], Z-D-Arg-D-Lys[Z-D-Arg], Z-Arg-D-Orn-[Z-Arg], Z-D-Arg-D-Orn[Z-D-Arg], (2-Cl-Z)-Arg-Lys[(2-Cl-Z)-Arg], (2-Cl-Z)-D-Arg-Lys[(2-Cl-Z)-D-Arg], (2-Cl-Z)-Arg-Orn[(2-Cl-Z)-Arg], (2-Cl-Z)-D-Arg-Orn [(2-Cl-Z)-D-Arg], (2-Cl-Z)-Arg-D-Lys-[(2-Cl-Z)-Arg], (2-Cl-Z)-D-Arg-D-Lys[(2-Cl-Z)-D-Arg], (2-Cl-Z)-Arg-D-Orn-[(2-Cl-Z)-Arg], (2-Cl-Z)-D-Arg-D-Orn[(2-Cl-Z)-D-Arg], $R^2$ is a substituent independently selected from the group comprising an amino substituent, a substituent derived from an amide or $C_{1-6}$alkyl ester of Phe, D-Phe, Tyr, D-Tyr, Ala, D-Ala, Gly, Ile, D-Ile, L and D-Trp by removing a hydrogen atom from an amino group, a substituent derived from $C_{1-6}$alkyl ester of a linear $C_{3-6}$aliphatic amino acid by removing a hydrogen atom from an amino group, as well as a substituent derived by removing a hydrogen atom from an amino group of a tryptamine, methylbenzylamine, benzylamine, nitrophenylamine, phenylamine, aminopyridine, histamine, $C_5$-$C_{22}$aliphatic amine, 7-aminocoumarin, cholesterylamine, or glucosamine molecule.

6. Compounds according to claim 5, which compounds are selected from the group consisting of:

the compound of the formula 2, wherein n is 4, P—$R^1$ is $N^\alpha$-2-chlorobenzyloxy-carbonyl-L-Arg and $R^2$ is a 3-aminopyridine moiety $C_5H_4N$—NH—, with the L-configuration on the chiral carbon atom linked to the —C(O)$R^2$ group, the compound of the formula 2, wherein n is 3, P—$R^1$ is $N^\epsilon$-chlorobenzyloxy-carbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 3, P—$R^1$ is $N^\alpha$-2-chlorobenzyloxy-carbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 2, P—$R^1$ is $N^\alpha$-2-chlorobenzyloxy-carbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 2, P—$R^1$ is $N^\epsilon$-2-chlorobenzyloxy-carbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 3, P—$R^1$ is $N^\alpha$-2-chlorobenzyloxy-carbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 1, P—$R^1$ is $N^\alpha$-2-chlorobenzyloxy-carbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 4, P—$R^1$ is $N^\alpha$-2-chlorobenzyloxy-carbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 4, P—$R^1$ is $N^\alpha$-benzyloxycarbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 4, P—$R^1$ is $N^\epsilon$-benzyloxycarbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 4, P—$R^1$ is $N^\alpha$-2-bromobenzyloxy-carbonyl-L-Lys and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 4, P—$R^1$ is $N^\alpha$-benzyloxycarbonyl-L-DAP and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 4, P—$R^1$ is $N^\alpha$-2-chlorobenzyloxy-carbonyl-L-Orn and $R^2$ is a tryptamine moiety $C_8H_6N$—$CH_2$—$CH_2$—NH—, with the L-configuration on the chiral carbon atom linked to the —C(O)$R^2$ group, in a hydrochloride salt form, the compound of the formula 2, wherein n is 3, P—$R^1$ is $N^\alpha$-2-chlorobenzyloxy-carbonyl-L-Lys and $R^2$ is a histamine moiety $C_3H_3N_2$—$CH_2$—$CH_2$—NH—, with the L-configuration on the chiral carbon atom linked to the —C(O)$R^2$ group, in a hydrochloride salt form, the compound of the formula 2, wherein n is 3, P—$R^1$ is $N^\epsilon$-2-chlorobenzyloxycarbonyl-L-Lys and $R^2$ is a histamine moiety $C_3H_3N_2$—$CH_2$—$CH_2$—NH—, with the L-configuration on the chiral carbon atom linked to the —C(O)R² group, in a hydrochloride salt form, and the compound of the formula 2, wherein n is 3, P—R¹ is N^α-2-chlorobenzyloxy-carbonyl-L-Lys and R² is a dodecylamine moiety $C_{12}H_{25}NH$—, with the L-configuration on the chiral carbon atom linked to the —C(O) R² group, in a hydrochloride salt form.

7. A hyperbranched core compound, of the formula 3

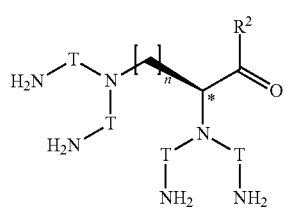

formula 3 comprising four -T-NH₂ branches, wherein n is an integer from 1 to 4 inclusive, wherein T is an alkylidene —$(CH_2)_2CONH(CH_2)_2$—group, and one R² branch, wherein R² is an —NH₂ group or a moiety derived from a primary organic amine molecule, by removing a hydrogen atom from an amino group.

8. The compound according to claim 7, of the formula 4

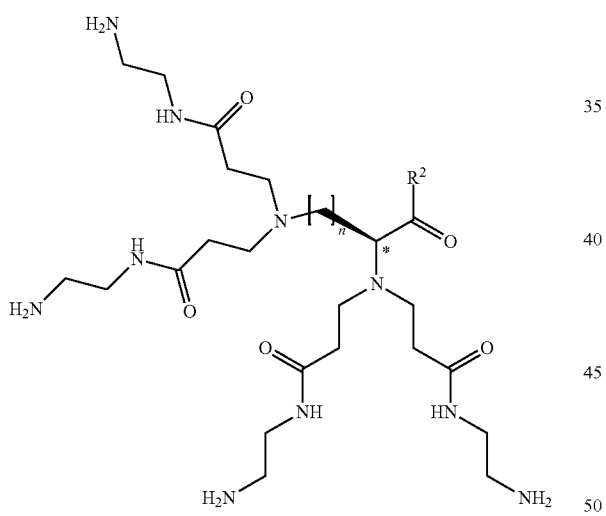

formula 4 wherein n is an integer of from 1 to 4 inclusive

R² is a substituent independently selected from the group comprising an —NH₂ group, a substituent derived from an amide or $C_{1-6}$alkyl ester of a natural amino acid by removing a hydrogen atom from an amino group, a substituent derived from $C_{1-6}$alkyl ester of a linear or branched chain non-natural $C_{3-6}$aliphatic amino acid by removing a hydrogen atom from an amino group, as well as a substituent derived by removing a hydrogen atom from an amino group of a tryptamine, benzylamine optionally substituted by alkyl, phenylamine optionally substituted by nitro, aminopyridine, histamine, $C_5$-$C_{22}$aliphatic amine, aminocoumarin, cholesterylamine, or glucosamine molecule.

9. Compound according to claim 8, wherein

R² is a substituent independently selected from the group comprising an —NH₂ group, a substituent derived from an amide or $C_{1-6}$alkyl ester of Phe, D-Phe, Tyr, D-Tyr, Ala, D-Ala, Gly, Ile, D-Ile, L and D-Trp by removing a hydrogen atom from an amino group, a substituent derived from $C_{1-6}$alkyl ester of a linear $C_{3-6}$aliphatic amino acid by removing a hydrogen atom from an amino group, as well as a substituent derived by removing a hydrogen atom from an amino group of a tryptamine, methylbenzylamine, benzylamine, nitrophenylamine, phenylamine, aminopyridine, histamine, $C_5$-$C_{22}$aliphatic amine, 7-aminocoumarin, cholesterylamine, or glucosamine molecule.

10. A process for the preparation of the dendrimeric compound comprising amino acids, characterized in that the process comprises reacting an amino acid compound, in the D, L form or a mixture of the D and L forms, of the formula 5

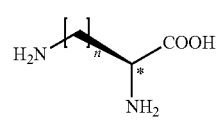

formula 5 wherein n is an integer of from 1 to 4 inclusive, with $C_{1-6}$ alkyl acrylate, optionally in the presence of a base, to yield a compound of the formula 6

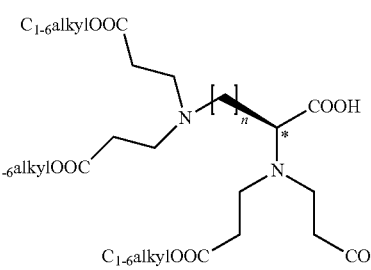

formula 6 followed by reacting the obtained compound of the formula 6, after optional acidification, with a primary organic amine or ammonia and the first coupling reagent to obtain an amide derivative of the formula 7

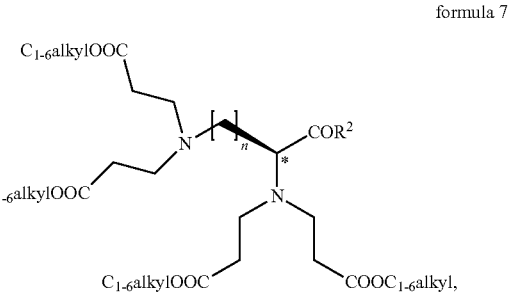

formula 7 which derivative of the formula 7 is subjected to aminolysis with ethylenediamine, to yield a branched core compound of the formula 3 formula 3

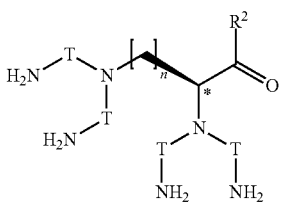

followed by coupling the compound of the formula 3, wherein T is —(CH$_2$)$_2$CONH(CH$_2$)$_2$-, and R$^2$ is an —NH$_2$ group or a moiety derived from a primary organic amine molecule by removing a hydrogen atom from an amino group, with an amino acid and/or peptide, wherein at least one hydrogen atom at least one amino group is optionally replaced by a protective group, in the presence of a second coupling reagent, to obtain a compound of the formula 1 formula 1

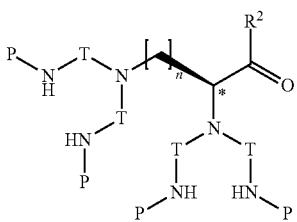

wherein R$^2$ and T have meanings as disclosed above, and P is an amino acid and/or peptide moiety derived from an amino acid/peptide molecule by removing a hydroxy group from a carboxy group, in which amino acid/peptide moiety at least one hydrogen atom of at least one amino group is optionally replaced by a protective group, optionally deprotecting the protected amino group and optionally converting into a pharmaceutically acceptable salt.

11. The process according to claim 10, characterized in that the compound of the formula 2 is obtained, formula 2

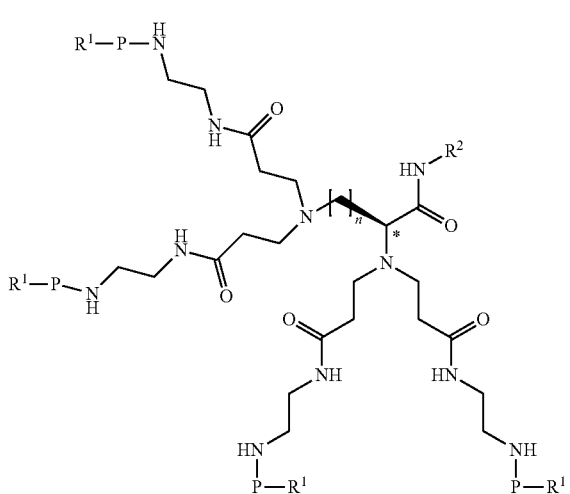

wherein
P is a moiety derived from an amino acid molecule, in the D or L form, by removing a hydroxy group from a carboxy group of lysine, ornithine, arginine, 1,4-diaminobutyric acid (DAB), 1,3-diaminopropionic acid (DAP), at least one hydrogen atom of at least one amino group being optionally replaced by an R$^1$ substituent, R$^1$ is a substituent independently selected from the group comprising a hydrogen atom (H), benzyloxycarbonyl (Z), 2-chlorobenzyloxycarbonyl (2-Cl-Z), 2-bromobenzyloxycarbonyl (2-Br-Z), 2-iodobenzyloxycarbonyl (2-I-Z), t-butyloxycarbonyl (Boc), fatty alkylcarbonyl, fatty alkenylcarbonyl, dansyl (DNS), naphthylsulfonyl, 9-fluorenylmethoxycarbonyl (Fmoc), and moieties derived by removing a hydroxy group from a carboxy group of the following molecules: Lysine (Lys), D-Lysine (D-Lys), Z-Lys, Z-D-Lys, Lys-(ε-Z), D-Lys-(ε-Z), (2-Cl-Z)-Lys, (2-Cl-Z)-D-Lys, Lys-(ε-2-Cl-Z), D-Lys-(ε-2-Cl-Z), DNS-(Lys), Lys-(ε-DNS), or Z-Arg, Z-D-Arg, (2-Cl-Z)-Arg, (2-Cl-Z)-D-Arg, Lys-(Z)Lys [Lys-(Z)], D-Lys-(Z)Lys[D-Lys-(Z)], Lys-(Z)Orn[Lys-(Z)], D-Lys-(Z)Orn[D-Lys-(Z)], Z-Lys-Lys-[Z-Lys], Z-Lys-D-Lys-[Z-Lys], Z-D-Lys-Lys-[Z-D-Lys], Z-D-Lys-D-Lys-[Z-D-Lys], derivatives with analogous sequences wherein the starting lysine moiety is replaced by an ornithine moiety (Orn), derivatives with analogous sequences wherein the starting lysine moiety is replaced by a 2,4-diaminobutyric acid (DAB) moiety, derivatives with analogous sequences wherein the starting lysine moiety is replaced by a 2,4-diaminopropionic acid (DAP) moiety, Z-Arg-Lys[Z-Arg], Z-D-Arg-Lys[Z-D-Arg], Z-Arg-Orn [Z-Arg], Z-D-Arg-Orn[Z-D-Arg], Z-Arg-D-Lys-[Z-Arg], Z-D-Arg-D-Lys[Z-D-Arg], Z-Arg-D-Orn-[Z-Arg], Z-D-Arg-D-Orn[Z-D-Arg], (2-Cl-Z)-Arg-Lys[(2-Cl-Z)-Arg], (2-Cl-Z)-D-Arg-Lys[(2-Cl-Z)-D-Arg], (2-Cl-Z)-Arg-Orn[(2-Cl-Z)-Arg], (2-Cl-Z)-D-Arg-Orn [(2-Cl-Z)-D-Arg],(2-Cl-Z)-Arg-D-Lys-[(2-Cl-Z)-Arg], (2-Cl-Z)-D-Arg-D-Lys[(2-Cl-Z)-D-Arg], (2-Cl-Z)-Arg-D-Orn-[(2-Cl-Z)-Arg], (2Cl-Z)-D-Arg-D-Orn[(2-Cl-Z)-D-Arg], R$^2$ is a substituent independently selected from the group comprising an amino substituent, a substituent derived from an amide or C$_{1-6}$alkyl ester of Phe, D-Phe, Tyr, D-Tyr, Ala, D-Ala, Gly, Ile, D-Ile, L and D-Trp by removing a hydrogen atom from an amino group, a substituent derived from C$_{1-6}$alkyl ester of a linear C$_{3-6}$aliphatic amino acid by removing a hydrogen atom from an amino group, as well as a substituent derived by removing a hydrogen atom from an amino group of a tryptamine, methylbenzylamine, benzylamine, nitrophenylamine, phenylamine, aminopyridine, histamine, C$_5$-C$_{22}$aliphatic amine, 7-aminocoumarin, cholesterylamine, or glucosamine molecule.

12. The process according to claim 11, characterized in that the first coupling reagent is a combination of N,N'-dicyclohexylcarbodiimide (DCC) and N-hydroxysuccinimide, and the second coupling reagent is a combination of N,N'-dicyclohexylcarbodiimide (DCC) and N-hydroxysuccinimide.

13. The process according to claim 11, characterized in that the reaction of the amino acid compound of the formula 5 with C$_{1-6}$alkyl acrylate is carried out in the presence of an alcoholic solvent.

14. The process according to claim 13, characterized in that the reaction is carried out at 60-90° C., for 24-48 hours.

15. A process for the preparation of a hyperbranched core compound, characterized in that the process comprises reacting an amino acid compound, in the D, L form or a mixture of the D and L forms, of the formula 5

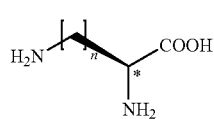

formula 5 wherein n is an integer of from 1 to 4 inclusive, with $C_{1-6}$alkyl acrylate, optionally in the presence of a base, to yield a compound of the formula 6

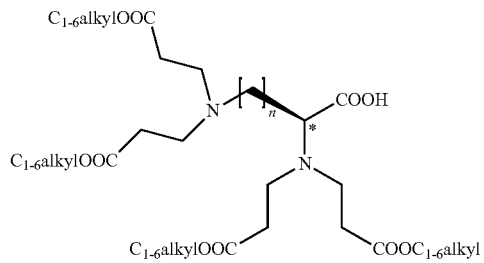

formula 6 followed by reacting the obtained compound of the formula 6, after optional acidification, with a primary organic amine or ammonia and a coupling reagent, to obtain an amide derivative of the formula 7

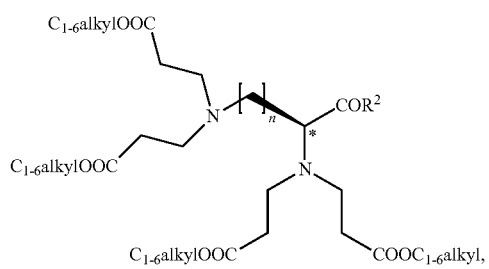

formula 7 which derivative of the formula 7 is subjected to aminolysis with ethylenediamine, to yield a branched core compound of the formula 3

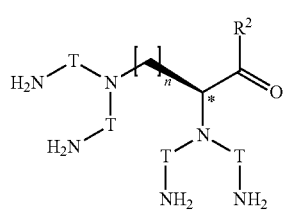

formula 3 wherein T is —$(CH_2)_2CONH(CH_2)_2$-, and $R^2$ is an —$NH_2$ group or a moiety derived from a primary organic amine molecule by removing a hydrogen atom from an amino group.

16. The process according to claim 15, characterized in that a compound of the formula 4 is obtained

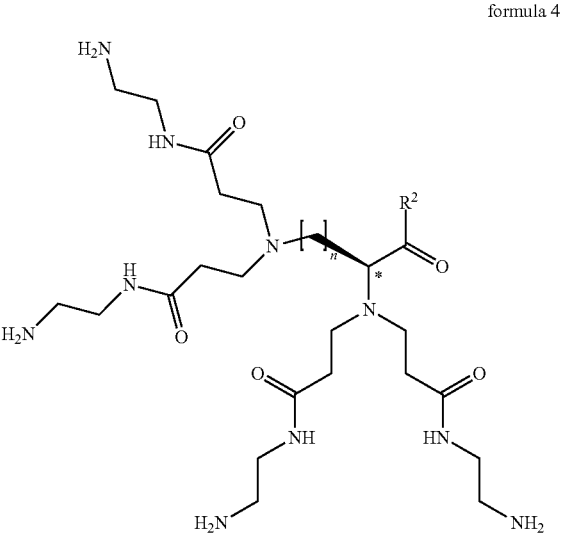

formula 4 wherein n is an integer of from 1 to 4 inclusive $R^2$ is a substituent independently selected from the group comprising an —$NH_2$ group, a substituent derived from an amide or $C_{1-6}$alkyl ester of Phe, D-Phe, Tyr, D-Tyr, Ala, D-Ala, Gly, Ile, D-Il e, L and D-Trp by removing a hydrogen atom from an amino group, a substituent derived from $C_{1-6}$alkyl ester of a linear $C_{3-6}$aliphatic amino acid by removing a hydrogen atom from an amino group, as well as a substituent derived by removing a hydrogen atom from an amino group of a tryptamine, methylbenzylamine, benzylamine, nitrophenylamine, phenylamine, aminopyridine, histamine, $C_5$-$C_{22}$aliphatic amine, 7-aminocoumarin, cholesterylamine, or glucosamine molecule.

17. The process according to claim 16, characterized in that the coupling reagent is a combination of N,N'-dicyclohexylcarbodiimide (DCC) and N-hydroxysuccinimide.

18. The process according to claim 16, characterized in that the reaction of the amino acid compound of the formula 5 with $C_{1-6}$alkyl acrylate is carried out in the presence of an alcoholic solvent.

19. The process according to claim 18, characterized in that the reaction is carried out at 60-90° C., for 24-48 hours.

20. A method for the treatment of a human or animal body with a dendrimeric compound comprising amino acids, the method comprising the administration of a medicament for bacterial cell growth inhibition, the medicament comprising the dendrimeric compound comprising amino acids of the formula 1 according to claim 1.

21. The method according to claim 20, characterized in that the dendrimeric compound of the formula 2 is used

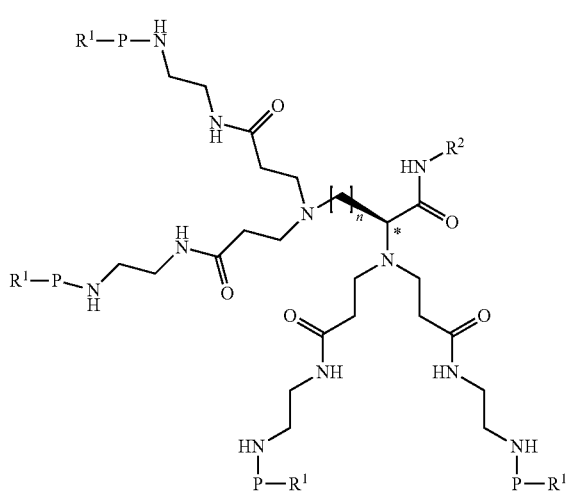

formula 2 wherein n is an integer of from 1 to 4 inclusive

P is a moiety derived from an amino acid molecule with two amino groups, by removing a hydroxy group from a carboxy group, at least one hydrogen atom of at least one amino group being optionally replaced by an $R^1$ substituent selected from the group comprising: fatty alkylcarbonyl, fatty alkenylcarbonyl, alkoxycarbonyl, arylalkoxycarbonyl optionally substituted on the aryl by halo, arylsulfonyl substituted on the aryl by an alkylamino group, a moiety derived from an amino acid molecule with two amino groups, by removing a hydroxy group from a carboxy group, at least one hydrogen atom of at least one amino group being optionally replaced by a substituent selected from the group comprising fatty alkylcarbonyl, fatty alkenylcarbonyl, alkoxycarbonyl, arylalkoxycarbonyl optionally substituted on the aryl by halo, arylsulfonyl substituted on the aryl by an alkylamino group, or a moiety derived from a lysine, ornithine, 2,4-diaminobutyric acid or 2,3-diaminopropionic acid amino acid molecule, by removing a hydroxy group from a carboxy group;

$R^2$ is a substituent independently selected from the group comprising an amino substituent, a substituent derived from an amide or $C_{1-6}$alkyl ester of a natural amino acid by removing a hydrogen atom from an amino group, a substituent derived from $C_{1-6}$alkyl ester of a linear or branched chain non-natural $C_{3-6}$aliphatic amino acid by removing a hydrogen atom from an amino group, as well as a substituent derived by removing a hydrogen atom from an amino group of a tryptamine, benzylamine optionally substituted by alkyl, phenylamine optionally substituted by nitro, aminopyridine, histamine, $C_5$-$C_{22}$aliphatic amine, aminocoumarin, or cholesterylamine molecule.

22. The method according to claim 21, characterized in that the compound of the formula 2 is used in the form of a cationic salt with a pharmaceutically acceptable anion, especially in the form of the hydrochloride salt.

23. The method according to claim 21, characterized in that the compound of the formula 2 is used, wherein:

n is an integer of from 1 to 4 inclusive,

P is a moiety derived from an amino acid molecule, in the D or L form, by removing a hydroxy group from a carboxy group of lysine, ornithine, arginine, 1,4-diaminobutyric acid (DAB), 1,3-diaminopropionic acid (DAP), at least one hydrogen atom of at least one amino group being optionally replaced by an $R^1$ substituent, $R^1$ is a substituent independently selected from the group comprising a hydrogen atom (H), benzyloxycarbonyl (Z), 2-chlorobenzyloxycarbonyl (2-Cl-Z), 2-bromobenzyloxycarbonyl (2-Br-Z), 2-iodobenzyloxycarbonyl (2-1-Z), t-butyloxycarbonyl (Boc), fatty alkylcarbonyl, fatty alkenylcarbonyl, dansyl (DNS), naphthylsulfonyl, 9-fluorenylmethoxycarbonyl (Fmoc), and moieties derived by removing a hydroxy group from a carboxy group of the following molecules: Lysine (Lys), D-Lysine (D-Lys), Z-Lys, Z-D-Lys, Lys-(ϵ-Z), D-Lys-(ϵ-Z), (2-Cl-Z)-Lys, (2-Cl-Z)-D-Lys, Lys-(ϵ-2-Cl-Z), D-Lys-(ϵ-2-Cl-Z), DNS-(Lys), Lys-(ϵ-DNS), or Z-Arg, Z-D-Arg, (2-Cl-Z)-Arg, (2-Cl-Z)-D-Arg, Lys-(Z)Lys [Lys-(Z)], D-Lys-(Z)Lys[D-Lys-(Z)], Lys-(Z)Orn[Lys-(Z)], D-Lys-(Z)Orn[D-Lys-(Z)], Z-Lys-Lys-[Z-Lys], Z-Lys-D-Lys-[Z-Lys], Z-D-Lys-Lys-[Z-D-Lys], Z-D-Lys-D-Lys-[Z-D-Lys], derivatives with analogous sequences wherein the starting lysine moiety is replaced by an ornithine moiety (Orn), derivatives with analogous sequences wherein the starting lysine moiety is replaced by a 2,4-diaminobutyric acid (DAB) moiety, derivatives with analogous sequences wherein the starting lysine moiety is replaced by a 2,4-diaminopropionic acid (DAP) moiety, Z-Arg-Lys[Z-Arg], Z-D-Arg-Lys[Z-D-Arg], Z-Arg-Orn [Z-Arg], Z-D-Arg-Orn[Z-D-Arg], Z-Arg-D-Lys-[Z-Arg], Z-D-Arg-D-Lys[Z-D-Arg], Z-Arg-D-Orn-[Z-Arg], Z-D-Arg-D-Orn[Z-D-Arg], (2-Cl-Z)-Arg-Lys[(2-Cl-Z)-Arg], (2-Cl-Z)-D-Arg-Lys[(2-Cl-Z)-D-Arg], (2-Cl-Z)-Arg-Orn[(2-Cl-Z)-Arg], (2-Cl-Z)-D-Arg-Orn [(2-Cl-Z)-D-Arg], (2-Cl-Z)-Arg-D-Lys-[(2-Cl-Z)-Arg], (2-Cl-Z)-D-Arg-D-Lys[(2-Cl-Z)-D-Arg], (2-Cl-Z)-Arg-D-Orn-[(2-Cl-Z)-Arg], (2Cl-Z)-D-Arg-D-Orn[(2-Cl-Z)-D-Arg], $R^2$ is a substituent independently selected from the group comprising an amino substituent, a substituent derived from an amide or $C_{1-6}$alkyl ester of Phe, D-Phe, Tyr, D-Tyr, Ala, D-Ala, Gly, lle, D-lle, L and D-Trp by removing a hydrogen atom from an amino group, a substituent derived from $C_{1-6}$alkyl ester of a linear $C_{3-6}$aliphatic amino acid by removing a hydrogen atom from an amino group, as well as a substituent derived by removing a hydrogen atom from an amino group of a tryptamine, methylbenzylamine, benzylamine, nitrophenylamine, phenylamine, aminopyridine, histamine, $C_5$-$C_{22}$aliphatic amine, 7-aminocoumarin, cholesterylamine, or glucosamine molecule.

24. The method according to claim 23, characterized in that the compound is selected from the group consisting of:

the compound of the formula 2, wherein n is 4, P—$R^1$ is $N^α$-2-chlorobenzyloxy-carbonyl-L-Arg and $R^2$ is a 3-aminopyridine moiety $C_5H_4N$—NH—, with the L-configuration on the chiral carbon atom linked to the —C(O)$R^2$ group, the compound of the formula 2, wherein n is 3, P—$R^1$ is $N^ϵ$-2-chlorobenzyloxy-carbonyl-L-Lys and $R^2$ is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 3, P—R¹ is $N^\alpha$-2-chlorobenzyloxy-carbonyl-L-Lys and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 2, P—R¹ is $N^\alpha$-2-chlorobenzyloxy-carbonyl-L-Lys and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 2, P—R¹ is $N^\epsilon$-2-chlorobenzyloxy-carbonyl-L-Lys and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 3, P—R¹ is $N^\alpha$-2-chlorobenzyloxy-carbonyl-L-Lys and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 1, P—R¹ is $N^\alpha$-2-chlorobenzyloxy-carbonyl-L-Lys and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 4, P—R¹ is $N^\alpha$-2-chlorobenzyloxycarbonyl-L-Lys and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 4, P—R¹ is $N^\alpha$-benzyloxycarbonyl-L-Lys and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 4, P—R¹ is $N^\epsilon$-benzyloxycarbonyl-L-Lys and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 4, P—R¹ is $N^\alpha$-2-bromobenzyloxy-carbonyl-L-Lys and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 4, P—R¹ is $N^\alpha$-benzyloxycarbonyl-L-DAP and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 4, P—R¹ is $N^\alpha$-2-chlorobenzyloxy-carbonyl-L-Orn and R² is a tryptamine moiety $C_8H_6N$—$CH_2$—$CH_2$—NH—, with the L-configuration on the chiral carbon atom linked to the —C(O)R² group, in a hydrochloride salt form, the compound of the formula 2, wherein n is 3, P—R¹ is $N^\alpha$-2-chlorobenzyloxy-carbonyl-L-Lys and R² is a histamine moiety $C_3H_3N_2$—$CH_2$—$CH_2$—NH—, with the L-configuration on the chiral carbon atom linked to the —C(O)R² group, in a hydrochloride salt form, the compound of the formula 2, wherein n is 3, P—R¹ is $N^\epsilon$-2-chlorobenzyloxy-carbonyl-L-Lys and R² is a histamine moiety $C_3H_3N_2$—$CH_2$—$CH_2$—NH—, with the L-configuration on the chiral carbon atom linked to the —C(O)R² group, in a hydrochloride salt form, and the compound of the formula 2, wherein n is 3, P—R¹ is $N^\alpha$-2-chlorobenzyloxy-carbonyl-L-Lys and R² is a dodecylamine moiety $C_{12}H_{25}NH$—, with the L-configuration on the chiral carbon atom linked to the —C(O)R² group, in a hydrochloride salt form.

25. A method for the preparation of macromolecular dendrimeric compounds comprising amino acids, the method comprising the step of coupling the hyperbranched core compound of the formula 3 according to claim 7 with an amino acid and/or peptide.

26. The method according to claim 25, characterized in that the hyperbranched core compound is a compound of the formula 4

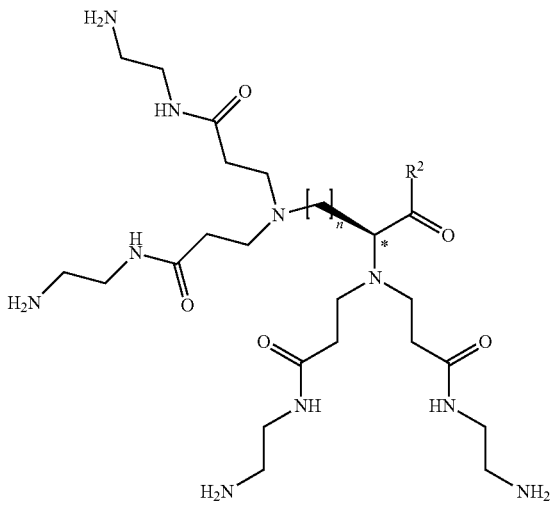

formula 4 wherein
n is an integer of from 1 to 4 inclusive
R² is a substituent independently selected from the group comprising an —$NH_2$ group, a moiety derived from an amide or $C_{1-6}$alkyl ester of a natural amino acid by removing a hydrogen atom from an amino group, a substituent derived from $C_{1-6}$alkyl ester of a linear or branched chain non-natural $C_{3-6}$aliphatic amino acid, as well as a substituent derived by removing a hydrogen atom from an amino group of a tryptamine, benzylamine optionally substituted by alkyl, phenylamine optionally substituted by nitro, aminopyridine, histamine, $C_5$-$C_{22}$aliphatic amine, aminocoumarin, cholesterylamine, or glucosamine molecule.

27. The method according to claim 26, characterized in that the compound of the formula 4 is used, wherein
R² is a substituent independently selected from the group comprising an —$NH_2$ group, a substituent derived from an amide or $C_{1-6}$alkyl ester of Phe, D-Phe, Tyr, D-Tyr, Ala, D-Ala, Gly, lle, D-lle, L and D-Trp by removing a hydrogen atom from an amino group, a substituent derived from $C_{1-6}$alkyl ester of a linear $C_{3-6}$aliphatic amino acid by removing a hydrogen atom from an amino group, as well as a substituent derived by removing a hydrogen atom from an amino group of a tryptamine, methylbenzylamine, benzylamine, nitrophenylamine, phenylamine, aminopyridine, histamine, $C_5$-$C_{22}$aliphatic amine, aminocoumarin, cholesterylamine, or glucosamine molecule.

28. A method for the treatment of a human or animal body with a dendrimeric compound comprising amino acids, the method comprising the administration of a medicament for melanoma cell growth inhibition, the medicament comprising the dendrimeric compound comprising amino acids of the formula 1 according to claim 6, and wherein the dendrimeric compound is selected from the group consisting of:

- the compound of the formula 2, wherein n is 3, P—$R^1$ is $N^\alpha$-2-chlorobenzyloxycarbonyl-L-Lys and $R^2$ is a tryptamine moiety $C_8H_6N$—$CH_2$—$CH_2$—NH—, with the L-configuration on the chiral carbon atom linked to the —$C(O)R^2$ group, in a hydrochloride salt form;
- the compound of the formula 2, wherein n is 4, P—$R^1$ is $N^\alpha$-2-chlorobenzyloxycarbonyl-L-Lys and $R^2$ is a tryptamine moiety $C_8H_6N$—$CH_2$—$CH_2$—NH—, with the L-configuration on the chiral carbon atom linked to the —$C(O)R^2$ group, in a hydrochloride salt form; and
- the compound of the formula 2, wherein n is 3, P—$R^1$ $N^\alpha$-2-chlorobenzyloxycarbonyl-L-Lys and $R^2$ is a dodecylamine moiety $C_{12}H_{25}NH$—, with the L-configuration on the chiral carbon atom linked to the —$C(O)R^2$ group, in a hydrochloride salt form.

* * * * *